US010815536B2

(12) United States Patent
Lipkin et al.

(10) Patent No.: US 10,815,536 B2
(45) Date of Patent: Oct. 27, 2020

(54) VIROME CAPTURE SEQUENCING PLATFORM, METHODS OF DESIGNING AND CONSTRUCTING AND METHODS OF USING

(71) Applicant: The Trustees of Columbia University in the City of New York, New York, NY (US)

(72) Inventors: Walter Ian Lipkin, New York, NY (US); Omar Jabado, Philadelphia, PA (US); Thomas Briese, White Plains, NY (US); Amit Kapoor, Columbus, OH (US); Jan Gogarten, Berlin (DE); Komal Jain, New York, NY (US); Nischay Mishra, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 201 days.

(21) Appl. No.: 15/759,937

(22) PCT Filed: Sep. 19, 2016

(86) PCT No.: PCT/US2016/052481
§ 371 (c)(1),
(2) Date: Mar. 14, 2018

(87) PCT Pub. No.: WO2017/049285
PCT Pub. Date: Mar. 23, 2017

(65) Prior Publication Data
US 2018/0265935 A1 Sep. 20, 2018

Related U.S. Application Data

(60) Provisional application No. 62/220,431, filed on Sep. 18, 2015.

(51) Int. Cl.
*C12Q 1/70* (2006.01)
*G16B 25/00* (2019.01)
*C12N 15/10* (2006.01)
*G16B 99/00* (2019.01)
*C40B 40/06* (2006.01)
*C40B 50/14* (2006.01)

(52) U.S. Cl.
CPC .......... *C12Q 1/70* (2013.01); *C12N 15/1006* (2013.01); *C40B 40/06* (2013.01); *C40B 50/14* (2013.01); *G16B 25/00* (2019.02); *G16B 99/00* (2019.02)

(58) Field of Classification Search
None
See application file for complete search history.

(56) References Cited

U.S. PATENT DOCUMENTS

2009/0105092 A1* 4/2009 Lipkin et al. ............ C12Q 1/70
506/16
2014/0227765 A1 8/2014 Nasar et al.

FOREIGN PATENT DOCUMENTS

WO WO 2006/073449 7/2006

OTHER PUBLICATIONS

Alva et al. (Jul. 2016) The MPI bioinformatics Toolkit as an integrative platform for advanced protein sequence and structure analysis. *Nucleic Acids Research*. pii: gkw348. PMID: 27131380).
Bent et al. Jul. 1, 2013. Enriching pathogen transcripts from infected samples: a capture-based approach to enhanced host-pathogen RNA sequencing. *Anal Biochem* 438:90-96.
Briese et al. Feb. 2005. Diagnostic system for rapid and sensitive differential detection of pathogens. *Emerg Infect Dis* 11:310-313.
Clark et al. Apr. 1, 2015. Quantitative gene profiling of long noncoding RNAs with targeted RNA sequencing. *Nature Methods* 12:339-342.
Kapoor et al. Apr. 9, 2013. Identification of rodent homologs of hepatitis C virus and pegiviruses. mBio 4:e00216-13.
Mercer et al. Apr. 4, 2014. Targeted sequencing for gene discovery and quantification using RNA CaptureSeq. *Nature Protocols* 9:989-1009.
Palacios et al. Jan. 2007. Panmicrobial oligonucleotide array for diagnosis of infectious diseases. *Emerg Infect Dis* 13:73-81.
Robinson et al. Jan. 2011. Integrative genomics viewer. *Nat Biotechnol* 29:24-26.
Saeed et al. Feb. 2003. TM4: a free, open-source system for microarray data management and analysis. *Biotechniques* 34:374-378.
Palacios, G el al., "Panmicrobial Oligonucleotide Array for Diagnosis of Infectious Diseases." Emerging Infectious Diseases. Jan. 2007, vol. 13, No. 1; pp. 73-81; p. 73, $2^{nd}$ column, 2nd-3rd paragraphs; p. 74 1st column, 1st and 4th pargraphs; p. 74, 2nd column, 3rd paragraph; p. 77. 1st column, 1st paragraph; DOI: 10.3201/eid1301.060837.
Briese, T et al., "Virome Capture Sequencing Enables Sensitive Viral Diagnosis and Comprehensive Virome Analysis.", mBio. Sep. 22, 2015, vol. 6, No. 5; e01491-15; entire document; DOI: 10.1128/mBio .01491-15.
Brown et al. Nov. 20, 2014. Seven strains of enterovirus D68 detected in the United States during the 2014 severe respiratory disease outbreak. *Genome Announc* 2:e01201-14.
Chevreux et al. Dec. 1999. Genome sequence assembly using trace signals and additional sequence information. *Comput Sci Biol* 99:45-56.
Depledge et al. Nov. 18, 2011. Specific capture and whole-genome sequencing of viruses from clinical samples. *PLoS One* 6:e27805.

(Continued)

*Primary Examiner* — Kaijiang Zhang
(74) *Attorney, Agent, or Firm* — Leason Ellis LLP

(57) ABSTRACT

The present invention provides novel methods, systems, tools, and kits for the simultaneous detection, identification and/or characterization of all viruses known or suspected to infect vertebrates. The methods, systems, tools, and kits described herein are based upon the virome capture sequencing platform ("VirCapSeq-VERT"), a novel platform developed by the inventors. The invention also provides methods and kits for designing and constructing of the virome capture sequencing platform.

22 Claims, 7 Drawing Sheets

(56) References Cited

OTHER PUBLICATIONS

Drexler et al. Sep. 2, 2014. Robustness against serum neutralization of a poliovirus type 1 from a lethal epidemic of poliomyelitis in the Republic of Congo in 2010. *Proc Natl Acad Sci U S A* 111:12889-12894.

Edgar, Aug. 12, 2010 Search and clustering orders of magnitude faster than BLAST. *Bioinformatics* 26(19):2460-2461.

Finn et al. May 18, 2011 HMMER Web Server: Interactive Sequence Similarity Searching. *Nucleic Acids Research* 39:W29-37.

Li and Godzik, Jul. 1, 2006. Cd-hit: a fast program for clustering and comparing large sets of protein or nucleotide sequences. *Bioinformatics* 22:1658-1659.

Li et al., 1000 Genome Project Data Processing Subgroup. May 30, 2009. The Sequence Alignment/Map format and SAMtools. *Bioinformatics* 25:2078-2079.

Luo et al. Dec. 27, 2012. SOAPdenovo2: an empirically improved memory-efficient short-read de novo assembler. *Gigascience* 1:18. 10.1186/2047-217X-1-18.

Schmieder and Edwards, Mar. 15, 2011. Quality control and preprocessing of metagenomic datasets. *BioInformatics* 27:863-864.

Tokarz et al. Sep. 2012. Worldwide emergence of multiple clades of enterovirus 68. *J Gen Virol* 93:1952-1958.

UniProt Consortium, Jan. 2015 UniProt: a Hub for protein information. *Nucleic Acids Research* 43:D204-D212. Published Online Oct. 27, 2014.

Wang et al. Nov. 26, 2002. Microarray-based detection and genotyping of viral pathogens. *Proc Natl Acad Sci U S A* 99:15687-15692.

* cited by examiner

Figure 3    Figure 3

Figure 3A  West Nile Virus — polyprotein CDS (1–10,945)

Figure 3B  Cache Valley virus, M-segment — polyprotein precursor CDS (1–4,463)

Figure 3C  MERS coronavirus — ORF1a CDS, ORF1aB CDS, ORF3 CDS, ORF4b CDS, ORF5 CDS, ORF8b CDS, E protein CDS, M protein CDS, N protein CDS (positions up to 30,113)

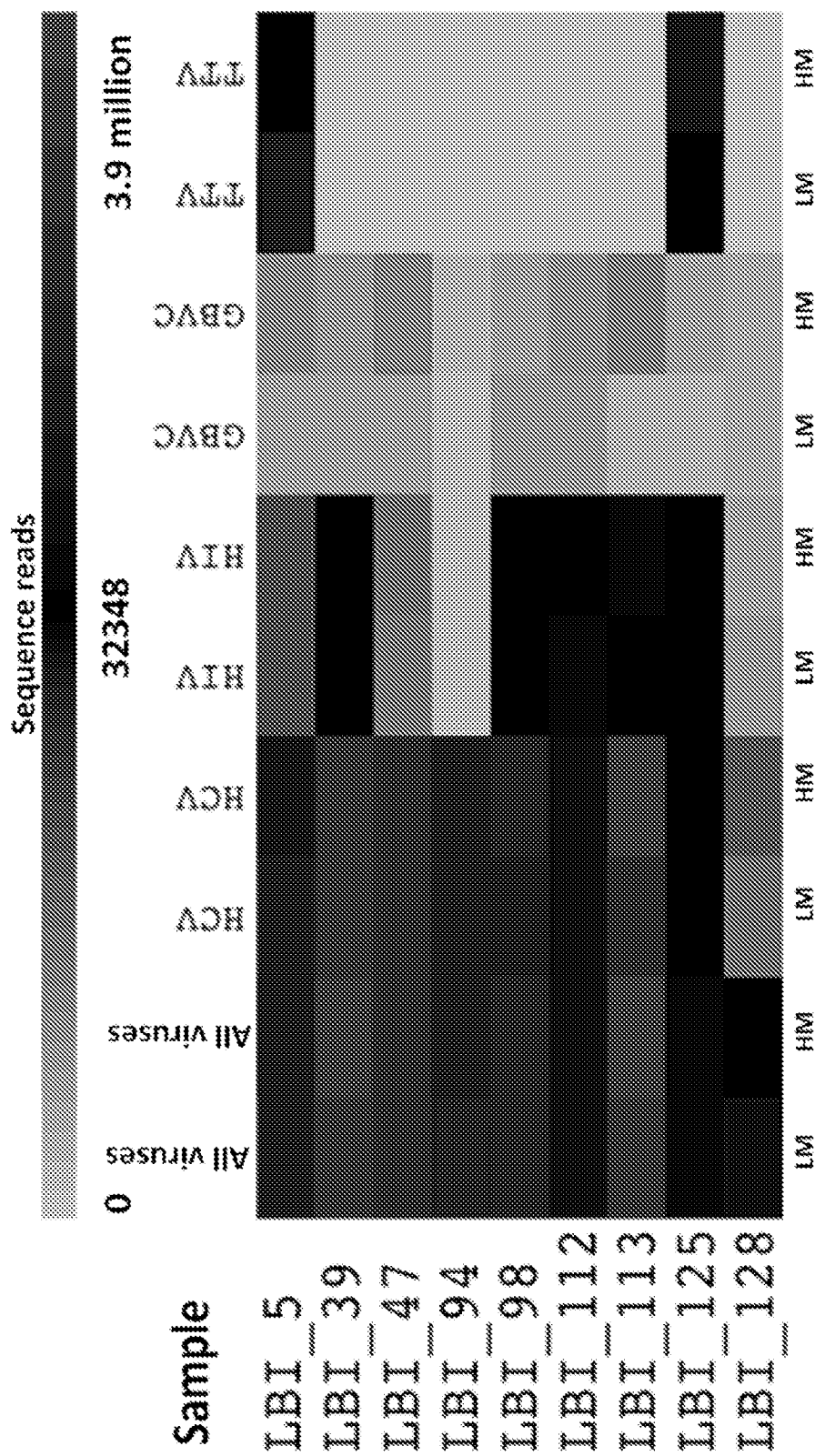

VIROME CAPTURE SEQUENCING PLATFORM, METHODS OF DESIGNING AND CONSTRUCTING AND METHODS OF USING

CROSS-REFERENCE TO OTHER APPLICATIONS

The present application is a U.S. National Phase Application under 35 U.S.C. § 371 of International Patent Application No. PCT/US2016/052481, filed Sep. 19, 2016, which claims priority to U.S. patent application Ser. No. 62/220,431 filed Sep. 18, 2015, each of which is hereby incorporated by reference as if expressly set forth in their respective entirety herein. The International Application was published in English on Mar. 23, 2017 as WO 2017/049285.

STATEMENT OF GOVERNMENT SUPPORT

This invention was made with government support under grants AI109761 and HL119485 awarded by the National Institutes of Health, and 2010-ST-061-AG0001 awarded by the Department of Homeland Security. The Government has certain rights in this invention.

FIELD OF THE INVENTION

This invention relates to the field of multiplex virus detection, identification, and characterization using high throughput sequencing.

BACKGROUND OF THE INVENTION

Clinical virology and virus discovery in the 20th century focused chiefly on the identification of viruses through microscopy, serology, and cell or animal infection studies (Kapoor and Lipkin 2001). With the advent of nucleic acid amplification, a wide range of molecular approaches for virus detection became available including various types of polymerase chain reaction (Mullis and Faloona 1987; Briese et al. 2005), microarrays (Wang et al. 2002; Palacios et al. 2007) and, most recently, high-throughput sequencing (HTS).

High throughput sequencing has enabled unbiased pathogen discovery and facilitated virome analyses that have enhanced our understanding of the origin, evolution, and ecology of known and novel viruses (Kapoor and Lipkin 2001). However, insensitivity, cost, and technical complexity have impeded the implementation of high-throughput nucleic acid sequencing in differential diagnosis of viral infections in clinical laboratories.

Unlike 16S rRNA of bacteria, viruses lack universally conserved markers and have plastic genomes that easily generate mutants, strains, and variants. Virus variants differing in sequence, even by a single point mutation, can vary in host range, transmissibility and pathogenicity (Guillot et al. 1994; Drexler et al. 2014). Accordingly, an ideal viral diagnostic platform should enable sensitive multiplexed detection of all viruses and their variants. Nucleic acid capture with oligonucleotides has been used to enhance the efficiency of HTS for characterizing host (Mercer et al. 2014; Clark et al. 2015) or selected microbial (Bent et al. 2013; Depledge et al. 2011) targets at low scale. However, such nucleic acid capture has not been successful with viruses. Strategies to increase the sensitivity of HTS have focused on the enrichment of viral template through subtraction of host nucleic acid via nuclease digestion and depletion of rRNA. Although they are helpful, none has achieved the sensitivity required for clinical applications. Thus, there is a need for a sensitive cost-effective capture sequencing platform for the detection of vertebrate viruses, especially in a clinical setting. The current invention solves this problem, and is a sensitive and specific HTS-based platform for clinical diagnosis and virome analysis of any type of sample.

SUMMARY OF THE INVENTION

The present invention provides novel methods, systems, tools, and kits for the simultaneous detection, identification and/or characterization of all viruses known or suspected to infect vertebrates. The methods, systems, tools, and kits described herein are based upon the virome capture sequencing platform ("VirCapSeq-VERT"), a novel platform developed by the inventors.

Accordingly, the present invention is a method of designing and/or constructing a virome capture sequencing platform utilizing a positive selection strategy for probes comprising nucleic acids derived from and/or present in the genome of viral taxa known or suspected to infect vertebrates, comprising the following steps.

The first step is to obtain sequence information from the genome of at least one virus from each viral taxa known or suspected to infect vertebrates. Table 1 comprises a list of viruses known to infect vertebrates. This list is over inclusive and comprehensive over what is known in the art. The list of viruses is cross-referenced with sequence information from databases.

The next step can comprise extracting the coding sequences. The coding sequences, i.e., protein sequences, of the viruses are extracted from the database clustered at about 80% sequence identity. In further embodiments, coding sequences are extracted that are clustered at about 85% identity, about 90% identity, about 95% identity, and about 96% identity.

In the next step, the coding sequences are broken into fragments from about 50 to 100 nucleotides in length. The oligonucleotides can be refined as to length and start/stop positions as required by $T_m$ and homopolymer repeats. The final $T_m$ of the oligonucleotides may range about no greater than about 75° C., more preferably no greater than about 65° C., and most preferably no greater than about 50° C.

Additionally, the fragments are tiled across the coding sequences at about 25 to 50 nucleotide intervals in order to cover all sequences in a database of about two million probes. If more probes are desired, the intervals can be smaller, less than 25 nucleotides down to about 1 nucleotide, to even overlapping probes. If less probes are desired in the platform, the interval can be larger, about 50 to 100 nucleotides.

Embodiments of the present invention also provide automated systems and methods for designing and/or constructing the virome capture sequencing platform. Models made by the embodiments of the present invention may be used by persons in the art to design and/or construct a virome capture sequencing platform.

In some embodiments of the present invention, systems, apparatuses, methods, and computer readable media are provided that use virus and sequence information along with analytic tools in a design model for designing and/or constructing the virome capture sequencing platform. For example, in some embodiments, a first analytical tool comprising information from Table 1 disclosing all of the viruses that infect vertebrates can be used to find pertinent sequence information and the pertinent sequence information processed using an algorithm to extract coding sequences and a second analytical tool to break the coding sequence into fragments for oligonucleotides with the proper parameters for the platform.

A further embodiment of the present invention is a novel platform otherwise known as the virome capture sequencing platform, designed and/or constructed using the method herein. In one embodiment, the platform comprises about between one million and three million probes, preferably about two million probes. In one embodiment, the probes are oligonucleotide probes. In a more preferred embodiment the oligonucleotide probes are synthetic. The platform can comprise and/or derive from the genomes of viral taxa known or suspected to infect vertebrates, including humans. In one embodiment, the platform can comprise the genomes of about 100, more preferably about 125, more preferably about 150, more preferably about 175, more preferably 200, and most preferably over 200 viral taxas known or suspected to infect vertebrates. In a preferred embodiment, the platform includes the viruses in Table 1. In one embodiment, the platform is in the form of an oligonucleotide library. In one embodiment, the oligonucleotides can comprise DNA, RNA, linked nucleic acids (LNA), bridged nucleic acids (BNA) or peptide nucleic acids (PNA) as well as any nucleic acids that can be derived naturally or synthesized now or in the future. In one embodiment the platform is in the form of a solution. In a further embodiment, the platform is in a solid state form such as a microarray or bead. In a further embodiment, the oligonucleotides are modified by a composition to facilitate binding to a solid state.

One embodiment of the current invention is a database comprising information on the virome capture sequencing platform including at least the length, nucleotide sequence, melting temperature, and viral origin of each oligonucleotide probe. A further embodiment is computer-readable storage mediums with program code comprising information, e.g., a database, comprising information regarding the virome capture sequencing platform including at least the length, nucleotide sequence, melting temperature, and viral origin of each oligonucleotide probe.

Additionally, the present invention provides a method for constructing a sequencing library for the detection, identification and/or characterization of at least one virus and preferably multiple viruses known or suspected to infect vertebrates using the virome capture sequencing platform in a positive selection scheme.

The present invention also provides systems for the simultaneous detection, identification and/or characterization of all viruses known or suspected to infect vertebrates, including those known and unknown, in any sample. The system includes at least one subsystem wherein the subsystem includes the virome capture sequencing platform of the invention. The system also can comprise subsystems for further detecting, identifying and/or characterizing of the virus, including but not limited to subsystems for preparation of the nucleic acids from the sample, hybridization, amplification, high throughput sequencing, and identification and characterization of the virus.

The present invention also provides methods for the simultaneous detection, identification and/or characterization of all viruses known or suspected to infect vertebrates in any sample utilizing the virome capture sequencing platform.

The present invention also provides for methods of detecting, identifying and/or characterizing an unknown virus in any sample, utilizing the novel virome capture sequencing platform.

A further embodiment is a kit for designing and/or constructing the virome capture sequencing platform comprising analytical tools to choose viral sequence information and break the coding sequences into fragments for oligonucleotides with the proper parameters for the platform.

A further embodiment is a kit for the detection, identification and/or characterization of all viruses known or suspected to infect vertebrates comprising the virome capture sequencing platform and optionally primers, enzymes, reagents, and/or user instructions for the further detection, identification and/or characterization of at least one virus in a sample.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 2 are graphs showing the results of high throughput sequencing using standard HTS and VirCapSeq-VERT. VirCapSeq-VERT enhances the performance of high throughput sequencing by increasing the number of mapped viral reads recovered from high background specimens. Eight different viral nucleic acids (NAs) were quantitated by qPCR and spiked into a background of lung (3 viruses) or blood (5 viruses) derived NA extracts. Samples were split in two and processed by standard HTS (left hand bars) or with VirCapSeq-VERT (right hand bars) (FIG. 2A).

FIG. 3 shows the read coverage versus the probe coverage of VirCapSeq-VERT for West Nile virus (FIG. 3A), Cache Valley virus (FIG. 3B), and MERS coronavirus (FIG. 3C). Virus genomes are represented by horizontal black lines and coding sequence by black pointed boxes at the bottom of each figure. The top graph of each figure indicates the read coverage obtained by VirCapSeq-VERT; probe coverage is shown below. Colored lines indicate mismatch to the reference used for alignment (green=A, red=T, blue=C, orange=G). Line heights indicate the frequency of the mismatched bases.

FIG. 7 is a heat map of the percentages of viral read numbers obtained from counting the number of reads mapping to contig sequences and unassembled singletons, calculated in relation to the total read number obtained using VirCapSeq-VERT. LM indicate samples processed as low multiplexing pool (9 samples). HM indicates samples processed as high multiplexing pool (23 samples).

DETAILED DESCRIPTION OF THE INVENTION

Molecular Biology

Figure 1A:
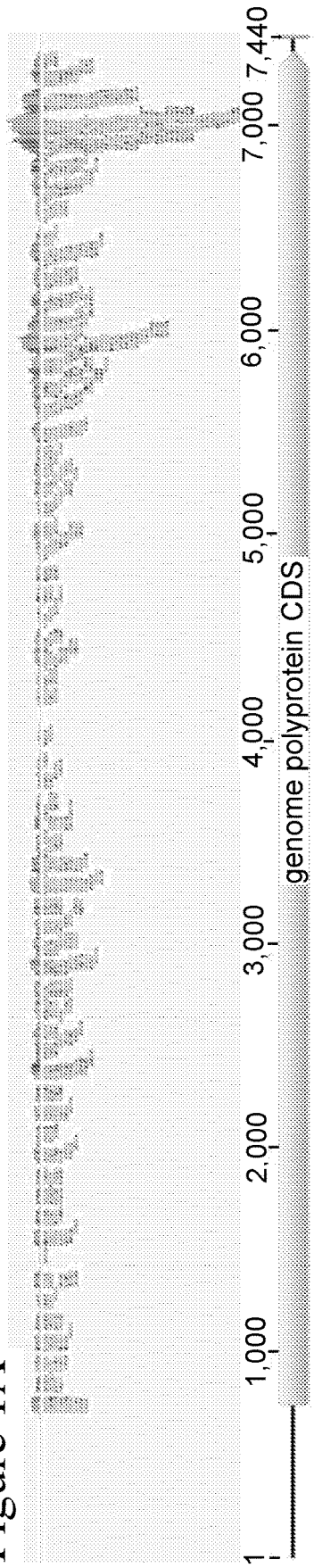
FIG. 1 show the results of in silico validation of VirCapSeq-VERT probe design. Probe depth and coverage of VirCapSeq-VERT probe library is shown for poliovirus (FIG. 1A), yellow fever virus (FIG. 1B), and parvovirus B19 (FIG. 1C). Virus genomes are represented by black lines, and the coding sequences by the pointed gray boxes at the bottom of the figure. The probes are indicated by gray boxes at the top of the figure. The top graph of each panel indicates probe depth at each locus. Colored lines in the probes indicate mismatch to the reference used for alignment (green=A, red=T, blue=C, orange=G). Line heights in the coverage track above indicate frequency of the mismatched bases.

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

As used herein and in the claims, the singular forms "a," "an," and "the" include the singular and the plural reference unless the context clearly indicates otherwise. Thus, for example, a reference to "an agent" includes a single agent and a plurality of such agents.

As used herein the terms "virome capture sequencing platform" and "VirCapSEQ-VERT" will be used interchangeably and refer to the novel capture sequencing platform of the current invention that allows the simultaneous detection, identification and/or characterization of all viruses known or suspected to infect vertebrates in any single sample in a single high throughput sequencing reaction. The terms denote the platform in every form, including but not limited to the collection of synthetic oligonucleotides representing the coding sequences of at least one virus from every viral taxa known to infect vertebrates (i.e., "probe library"), either in solution or attached to a solid support, a database comprising information on the virome capture sequencing platform including at least the length, nucleotide sequence, melting temperature, and viral origin of each oligonucleotide probe, and computer-readable storage mediums with program code comprising information on the virome capture sequencing platform including at least the length, nucleotide sequence, melting temperature, and viral origin of each oligonucleotide probe.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject.

The term "detection", "detect", "detecting" and the like as used herein means as used herein means to discover the presence or existence of.

The terms "identification", "identify", "identifying" and the like as used herein means to recognize a specific virus or viruses in sample from a subject.

The term "characterization", "characterize", "characterizing" and the like as used herein means to describe or categorize by features, in some cases herein by sequence information.

As used herein, the term "isolated" and the like means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, an isolated genomic DNA, or a restriction fragment. In another embodiment, an isolated nucleic acid is preferably excised from the chromosome in which it may be found. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated material may be, but need not be, purified.

As used herein, a "nucleic acid", and "polynucleotide" and "nucleic acid sequence" and "nucleotide sequence" includes a nucleic acid, an oligonucleotide, a nucleotide, a polynucleotide, and any fragment, variant, or derivative thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. As further used herein, the term "cDNA" refers to an isolated DNA polynucleotide or nucleic acid molecule, or any fragment, derivative, or complement thereof. It may be double-stranded, single-stranded, or triple-stranded, it may have originated recombinantly or synthetically, and it may represent coding and/or noncoding 5' and/or 3' sequences.

The term "fragment" when used in reference to a nucleotide sequence refers to portions of that nucleotide sequence. The fragments may range in size from 5 nucleotide residues to the entire nucleotide sequence minus one nucleic acid residue.

The term "genome" as used herein, refers to the entirety of an organism's hereditary information that is encoded in its primary DNA or RNA or nucleotide sequence (DNA or RNA as applicable). The genome includes both the genes and the non-coding sequences. For example, the genome may represent a viral genome, a microbial genome or a mammalian genome.

As used herein, the term "gene" means the deoxyribonucleotide or ribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both amplified and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "sequencing library", as used herein refers to a library of nucleic acids that are compatible with next-generation high throughput sequencers.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. The nucleic acids that comprises the oligonucleotides include but are not limited to DNA, RNA, linked nucleic acids (LNA), bridged nucleic acids (BNA) and peptide nucleic acids (PNA). Oligonucleotides can be labeled, e.g., with $^{32}P$-nucleotides or nucleotides to which a label, such as biotin, has been covalently conjugated.

The term "synthetic oligonucleotide" refers to single-stranded DNA or RNA molecules having preferably from about 10 to about 100 bases, which can be synthesized. In general, these synthetic molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA or RNA molecules having a designed or desired nucleotide sequence.

The term "identifier" as used herein refers to any unique, non-naturally occurring, nucleic acid sequence that may be used to identify the originating genome of a nucleic acid fragment. The identifier function can sometimes be combined with other functionalities such as adapters or primers and can be located at any convenient position.

The term "DNA sequencing" as used herein, refers to any methods for determining the order of the nucleotide bases—adenine, guanine, cytosine, and thymine—in a molecule of DNA.

The terms "next-generation sequencing platform" and "high-throughput sequencing" and "HTS" as used herein, refer to any nucleic acid sequencing device that utilizes massively parallel technology. For example, such a platform may include, but is not limited to, Illumina sequencing platforms.

As used herein, the terms "complementary" or "complementarity" are used in reference to "polynucleotides" and "oligonucleotides" (which are interchangeable terms that refer to a sequence of nucleotides) related by the base-pairing rules. It may also include mimics of or artificial bases that may not faithfully adhere to the base-pairing rules. For example, the sequence "C-A-G-T," is complementary to the sequence "G-T-C-A." Complementarity can be "partial" or "total." "Partial" complementarity is where one or more nucleic acid bases are not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The term "nucleic acid hybridization" or "hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid).

As used herein the term "hybridization product" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization product may be formed in solution or between one nucleic acid sequence present in solution and another nucleic acid sequence immobilized to a solid support.

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: Nucleic Acid Hybridization (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

"Amplification" is defined as the production of additional copies of a nucleic acid sequence and is generally carried out either in vivo, or in vitro, i.e. for example using polymerase chain reaction.

As used herein, the term "polymerase chain reaction" ("PCR") refers to the method disclosed in U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $_{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. With PCR, it is also possible to amplify a complex mixture (library) of linear DNA molecules, provided they carry suitable universal sequences on either end such that universal PCR primers bind outside of the DNA molecules that are to be amplified.

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin. Sequence identity can be determined using any of a number of publicly available sequence comparison algorithms, such as BLAST, FASTA, DNA Strider, and GCG (Genetics Computer Group, Program Manual for the GCG Package, Version 7, Madison, Wis.).

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The Virome Capture Sequencing Platform

The current invention includes a method of designing and/or constructing a capture sequencing platform, the platform itself, and methods of using the platform to construct sequencing libraries suitable for sequencing in any high throughput sequencing technology. The invention also includes methods and systems for simultaneously detecting all of the viruses known or suspected to infect vertebrates in a single sample, of any origin, using the novel capture sequencing platform. The present invention, denoted virome capture sequencing platform for vertebrate viruses, or Vir-CapSeq-VERT, increases the sensitivity of sequence-based virus detection and characterization over current methods in the prior art. It enables detection of viral sequences in any complex sample backgrounds, including those found in clinical specimens. The highly multiplexed nature of the system allows both the simultaneous identification and the comprehensive genetic characterization of all known vertebrate viruses, their genetic variants, and novel sequences. The operational simplicity and efficiency of the virome capture sequencing platform may facilitate transition of high throughput sequencing to clinical diagnostic as well as research applications.

The platform is based upon a strategy for the enrichment of sequences of all viruses known or suspected to infect vertebrates, including humans, and includes sequences of variants and mutants of the viruses.

Current virus diagnostic assays that are commonly based on PCR assays targeting one or a few specific agents may fail to detect virus variants and provide only limited genotypic information. The invention provided herein addresses many of the current challenges of PCR and HTS for diagnostics and virome analysis. The sensitivity and specificity of the virome capture sequencing platform are comparable to those of agent-specific real-time PCR (see Table 6). The current methods and systems use a positive selection method for high throughput (HTS) screening for microbial diagnostic and whole-virome analysis. Additionally, the 100- to 10,000-fold increase achieved in on-target reads enables leveraging of sequencing depth against costs in research applications. The approximately per-sample cost of 40 U.S. dollars (USD) of the virome capture sequencing platform in a 20 barcode sample format compares favorably with costs of other enrichment procedures, such as rRNA depletion (approximately 65 USD per sample), particularly given its advantages in sensitivity, genome coverage, and ease of use. The capacity for highly multiplexed sample processing and simplified sample handling is cost-effective and reduces the risk of cross contamination.

Additionally, while the virome capture sequencing platform is not specifically designed for viral discovery, nonetheless, it enables sequencing of genomes with as little as 75% overall sequence identity. Results of rotavirus and hepacivirus analyses indicate that where the goal is detection rather than comprehensive genome sequencing, the capture sequencing platform has the potential, through hybridization to conserved regions, to detect novel viruses with an overall nucleotide divergence in the range of 40% (see Example 5).

In summary, the virome capture sequencing platform is a powerful tool for diagnostic and research applications. It has sensitivity similar to that obtained with targeted real-time PCR, with the advantage of detecting viral variants that would not be captured with specific PCR assays as well as the potential to provide the complete genome coverage needed for assessment of viral diversity and evolution for epidemiological and public health applications. The method is inexpensive. Furthermore, as the vast majority of sequences will represent viral rather than host template, contig assembly and BLAST analyses will be less computationally intensive and require less time to complete than brute force, unbiased sequencing.

Accordingly, the present invention is a method of designing and/or constructing a sequence capture platform or technology otherwise known as virome capture sequencing platform or VirCapSeq-VERT. The present invention is a method of designing and/or constructing a sequence capture platform that comprises oligonucleotide probes selectively enriched for all viruses that infect vertebrates, and the resulting capture sequence platform. Accordingly the method may include the following steps.

The first step is to obtain sequence information from the genome of at least one virus from each viral taxa known to infect vertebrates. The curation of the list of these viral taxa was performed based upon the work and unique knowledge of the inventors in the field of vertebrate viruses. In one embodiment, the viral taxa listed in Table 1 are used for obtaining sequence data. The list of viruses in Table 1 is over inclusive as to viruses known in the art to infect vertebrates. In a further embodiment, new viruses that are discovered to infect vertebrates can be included as well.

Sequence information for viruses is obtained from databases such as EMBL Coding Domain Sequence database, NCBI Genbank and any public or private database of sequence information.

The second step of the method is to extract the coding sequences from the database for use in designing the oligonucleotides. This is in contrast to the use of the entire genome of the virus which would include many more sequences and be less efficient. In one embodiment, coding sequences clustered at about 80% sequence identity are used. In a more preferred embodiment, coding sequences clustered at about 85% sequence identity are used. In a more preferred embodiment, coding sequences clustered at about 90% sequence identity are used. In a more preferred embodiment, coding sequences clustered at about 95% sequence identity are used. In a most preferred embodiment, coding sequences clustered at about 96% sequence identity are used. Computer algorithms can be used for choosing the coding sequences, including but not limited to CD-Hit (Li and Godzik 2006), MOI Bioinformatics Toolkit (Alva et al. 2016), HMMer (Finn et al. 2011), and UCLUST (Edgar 2010). Also a complete non-redundant database could be used such as the UniProt (2015).

The next step of the method is to break the sequences into fragments to be the basis of the oligonucleotides. The fragments are from about 50 to 100 nucleotides in length. The oligonucleotides can be refined as to length and start/stop positions as required by $T_m$ and homopolymer repeats.

For example, the final $T_m$ of the oligonucleotides should be similar and not too broad in range. It is preferred that the final $T_m$ of all of the oligonucleotides in the platform should be in a range of about no greater than about 75° C., more preferably no greater than about 65° C., and most preferably no greater than about 50° C. The final $T_m$ of the oligonucleotides in the exemplified platform ranged from about 58° C. to about 101° C. Thus, the fragment size can be adjusted accordingly to obtain oligonucleotides with the suitable melting temperatures.

To address sequence variation and capture variant or mutated sequences, sequences are retained if they diverge about 10%, i.e, have about 90% identity.

As used herein a variant of the sequence has at least about 90%, about 95%, about 95.5%, about 96%, about 96.5%, about 97%, about 97.5%, about 98%, about 98.5%, about 99%, or about 99.5% or about 99.9% identity to a nucleic acid sequence.

As used herein the term "mutated" means any detectable change in genetic material including DNA and RNA. A "mutant" means a gene, expression product or virus with a change in genetic material.

Additionally, the fragments are tiled across the coding sequences at about 25 to 50 nucleotide intervals in order to cover all sequences in a database of about two million probes. If more probes are desired, the intervals can be smaller, less than 25 nucleotides down to about 1 nucleotide, to even overlapping probes. If less probes are desired in the platform, the interval can be larger, about 50 to 100 nucleotides.

The present invention also relates to methods and systems that use computer-generated information to design and/or construct a virome capture sequencing platform. For example, in some embodiments, a first analytical tool using the information from Table 1 disclosing all of the viruses that infect vertebrates can be used to find pertinent sequence information and the pertinent sequence information processed using an algorithm to extract coding sequences and a second analytical tool to fragment the coding sequences into oligonucleotides with the proper parameters for the platform including proper length, melting temperature, GC distribution, distance spaced between the oligonucleotides on the coding sequences, and percentage sequence identity.

In a further aspect of the present invention, analytical tools such as a first module configured to perform the choice of coding sequences from the proper viruses and a second module to perform the fragmentation of the coding sequences may be provided that determines features of the oligonucleotides such as the proper length, melting temperature, GC distribution, distance spaced between the oligonucleotides on the coding sequences, and percentage sequence identity. The results of these tools form a model for use in designing the oligonucleotides for the virome capture sequencing platform.

An illustrative system for generating a design model includes an analytical tool such as a module configured to include viruses from Table 1 and a database of sequence information. The analytical tool may include any suitable hardware, software, or combination thereof for determining correlations between the viruses from Table 1 and the sequence data from database. Once the pertinent sequence data from the database is chosen, a known algorithm is used to extract the coding sequences clustered at about 80% identity, or in other embodiments, clustered at about 85% identity, about 90% identity, about 95% identity, and about 96% identity. A second analytical tool such as module is used to fragment the coding sequences. This analytical tool may include any suitable hardware, software, or combination for determining the necessary features of the oligonucleotides of the virome capture sequencing platform including proper length, melting temperature, GC distribution, distance spaced between the oligonucleotides on the coding sequences, and percentage sequence identity. In some embodiments of the invention, the features of the oligonucleotides are about 50 to 100 nucleotides in length, melting temperature ranging about no greater than about 75° C., more preferably no greater than about 65° C., and most preferably no greater than about 50° C., spaced at about 25 to 50 nucleotides intervals across coding sequences, and about 90% sequence identity.

After the sequence information is obtained for the oligonucleotides, the oligonucleotides can be synthesized by any method known in the art including but not limited to solid-phase synthesis using phosphoramidite method and phosphoramidite building blocks derived from protected 2'-deoxynucleosides (dA, dC, dG, and T), ribonucleosides (A, C, G, and U), or chemically modified nucleosides, e.g. linked nucleic acids (LNA), bridged nucleic acids (BNA) or peptide nucleic acids (PNA).

The oligonucleotides can be refined as to length and start/stop positions as required by $T_m$ and homopolymer repeats. The final $T_m$ of the oligonucleotides may range about no greater than about 75° C., more preferably no greater than about 65° C., and most preferably no greater than about 50° C. These parameters can be refined as is known in the art. A final library designed the method of the present invention comprised about 1,993,176 oligonucleotides ranging in length from 50 to 100 nt, with a mean length of 74.3 and a median length of 74 with a $T_m$ ranging from 58.7° C. to 101° C., with a mean $T_m$ of 79.69° C. and median $T_m$ of 79.1° C. The distribution of GC content in percentages was GC % 0.44 mean and 0.42 median with a range of 0 to 1.

A preferred embodiment of the platform is a library comprising the oligonucleotide probes that are capable of capturing nucleic acids from at least one virus from every taxa known or suspected to infect vertebrates.

In one embodiment, the oligonucleotides of the platform are in solution.

In one embodiment of the present invention, the oligonucleotides comprising the capture sequence platform are pre-bound to a solid support or substrate. Preferred solid supports include, but are not limited to, beads (e.g., magnetic beads (i.e., the bead itself is magnetic, or the bead is susceptible to capture by a magnet) made of metal, glass, plastic, dextran (such as the dextran bead sold under the tradename, Sephadex (Pharmacia)), silica gel, agarose gel (such as those sold under the tradename, Sepharose (Pharmacia)), or cellulose); capillaries; flat supports (e.g., filters, plates, or membranes made of glass, metal (such as steel, gold, silver, aluminum, copper, or silicon), or plastic (such as polyethylene, polypropylene, polyamide, or polyvinylidene fluoride)); a chromatographic substrate; a microfluidics substrate; and pins (e.g., arrays of pins suitable for combinatorial synthesis or analysis of beads in pits of flat surfaces (such as wafers), with or without filter plates). Additional examples of suitable solid supports include, without limitation, agarose, cellulose, dextran, polyacrylamide, polystyrene, sepharose, and other insoluble organic polymers. Appropriate binding conditions (e.g., temperature, pH, and salt concentration) may be readily determined by the skilled artisan.

The oligonucleotides comprising the capture sequence platform may be either covalently or non-covalently bound to the solid support. Furthermore, the oligonucleotides comprising the sequence capture platform may be directly bound to the solid support (e.g., the oligonucleotides are in direct van der Waal and/or hydrogen bond and/or salt-bridge contact with the solid support), or indirectly bound to the solid support (e.g., the oligonucleotides are not in direct contact with the solid support themselves). Where the oligonucleotides comprising the sequence capture platform are indirectly bound to the solid support, the nucleotides of the capture nucleic acid are linked to an intermediate composition that, itself, is in direct contact with the solid support.

To facilitate binding of the oligonucleotides comprising the capture sequence platform to the solid support, the oligonucleotides comprising the capture sequence platform may be modified with one or more molecules suitable for direct binding to a solid support and/or indirect binding to a solid support by way of an intermediate composition or spacer molecule that is bound to the solid support (such as an antibody, a receptor, a binding protein, or an enzyme). Examples of such modifications include, without limitation, a ligand (e.g., a small organic or inorganic molecule, a ligand to a receptor, a ligand to a binding protein or the binding domain thereof (such as biotin and digoxigenin)), an antigen and the binding domain thereof, an apatamer, a peptide tag, an antibody, and a substrate of an enzyme. In a preferred embodiment, the oligonucleotides comprise biotin.

Linkers or spacer molecules suitable for spacing biological and other molecules, including nucleic acids/polynucleotides, from solid surfaces are well-known in the art, and include, without limitation, polypeptides, saturated or unsaturated bifunctional hydrocarbons, and polymers (e.g., polyethylene glycol). Other useful linkers are commercially available.

In one embodiment of the present invention, a sequence of the oligonucleotides comprising the capture sequence platform are the complement of (i.e., is complementary to) a sequence of genome of a virus known to infect vertebrates. In another embodiment, the oligonucleotides comprising the capture sequence platform are capable of hybridizing to a sequence of genome of a virus known to infect vertebrates under high-stringency conditions. The "complement" of a nucleic acid sequence refers, herein, to a nucleic acid molecule which is completely complementary to another nucleic acid, or which will hybridize to the other nucleic acid under conditions of high stringency. High-stringency conditions are known in the art. See, e.g., Maniatis et al., Molecular Cloning: A Laboratory Manual, 2nd ed. (Cold Spring Harbor: Cold Spring Harbor Laboratory, 1989) and Ausubel et al., eds., Current Protocols in Molecular Biology (New York, N.Y.: John Wiley & Sons, Inc., 2001). Stringent conditions are sequence-dependent, and may vary depending upon the circumstances.

In the exemplified embodiment, the oligonucleotides comprising the capture sequence platform are synthesized using a cleavable programmable array wherein the array comprises the oligonucleotides comprising the sequence capture platform. The oligonucleotides are cleaved from the array and hybridized with the nucleic acids from the sample in solution.

The present invention also includes the sequence capture platform otherwise known as virome capture sequencing platform made from the method of the invention. The platform comprises about 1,993,176 oligonucleotides ranging in length from 50 to 100 nt and with a $T_m$ from 58.7° C. to 101° C. The oligonucleotides comprise sequences from the genome of at least one virus for every viral taxa known to infect vertebrates (Table 1). Additionally, the sequence capture platform comprises sequences that will capture variants and mutants from the viral taxa.

The virome capture sequencing platform of the present invention can be in the form of a collection of oligonucleotides, preferably designed as set forth above, i.e., a probe library. The oligonucleotides can be in solution or attached to a solid state, such as an array or a bead. Additionally, the oligonucleotides can be modified with another molecule. In a preferred embodiment, the oligonucleotides comprise biotin.

The virome capture sequencing platform can also be in the form of a database or databases which can include information regarding the sequence and length and $T_m$ of each oligonucleotide probe, and the virus from which the oligonucleotide sequence derived. The database can searchable. From the database, one of skill in the art can obtain the information needed to design and synthesis the oligonucleotide probes comprising the virome capture sequencing platform. The databases can also be recorded on machine-readable storage medium, any medium that can be read and accessed directly by a computer. A machine-readable storage medium can comprise, for example, a data storage material that is encoded with machine-readable data or data arrays. Machine-readable storage medium can include but are not limited to magnetic storage media, optical storage media, electrical storage media, and hybrids. One of skill in the art can easily determine how presently known machine-readable storage medium and future developed machine-readable storage medium can be used to create a manufacture of a recording of any database information. "Recorded" refers to a process for storing information on a machine-readable storage medium using any method known in the art.

Construction of a Sequencing Library

A further embodiment of the present invention is a method of constructing a sequencing library suitable for sequencing with any high throughput sequencing method utilizing the novel virome capture sequencing platform.

Accordingly the method may include the following steps.

Nucleic acid from a sample is obtained. The sample used in the present invention may be an environmental sample, a food sample, or a biological sample. The preferred sample is a biological sample. A biological sample may be obtained from a tissue of a subject or bodily fluid from a subject including but not limited to nasopharyngeal aspirate, blood, cerebrospinal fluid, saliva, serum, urine, sputum, bronchial lavage, pericardial fluid, or peritoneal fluid, or a solid such as feces. A biological sample can also be cells, cell culture or cell culture medium. The sample may or may not comprise or contain any viral nucleic acids. In a preferred embodiment, the sample is from a vertebrate subject, and in a most preferred embodiment, the sample is from a human subject. In another preferred embodiment, the sample comprises blood and is being tested prior to transfusion. In another preferred embodiment, the sample comprises cells, cell culture, cell culture medium or any other composition being used for developing pharmaceutical and therapeutic agents.

The nucleic acids from the sample are subjected to fragmentation, to obtain a nucleic acid fragment. There are no special limitations on a type of the nucleic acid sample which may be used and there are no special limitations on means for performing the fragmentation; and any chemical or physical methods which may make nucleic acid samples subjected to randomly fragmentation may be used to randomly fragment the nucleic acid sample. It is preferred that the nucleic acid sample is fragmented to obtain a nucleic acid fragment having a length of 200 bp to 300 bp or any other size distribution suitable for the respective sequencing platform.

After being obtained, the nucleic acid fragments can be ligated to an adaptor. In one embodiment, the adaptor is a linear adaptor. Linear adaptors can be added to the fragments by end-repairing the fragments, to obtain an end-repaired fragment; adding an adenine base to the 3' ends of the fragment, to obtain a fragment having an adenine at the 3' end; and ligating an adaptor to the fragment having an adenine at the 3' end.

In some embodiments, the adaptor comprises an identifier sequence. In some embodiments, the adaptor comprises sequences for priming for amplification. In some embodiments, the adaptor comprises both an identified sequence and sequences for priming for amplification.

After the nucleic acid fragment is ligated to the adaptor, it is contacted with the oligonucleotides of the virome capture sequencing platform, under conditions that allow the nucleic acid fragment to hybridize to the oligonucleotides of the virome capture sequencing platform if the nucleic acid comprises any viral sequences derived from any virus known or suspected to infect vertebrates. This step may be performed in solution or in a solid phase hybridization method, depending on the form of the virome capture sequencing platform.

After contact with the oligonucleotides of the virome capture sequencing platform, any hybridization product(s) may be subject to amplification conditions. In one embodiment, the primers for amplification are present in the adaptor ligated to the nucleic acid fragment. The resulting amplified product(s) comprise the sequencing library that is suitable to be sequenced using any HTS system now known or later developed.

Amplification may be carried out by any means known in the art, including polymerase chain reaction (PCR) and isothermal amplification. PCR is a practical system for in vitro amplification of a DNA base sequence. For example, a PCR assay may use a heat-stable polymerase and two primers: one complementary to the (+)-strand at one end of the sequence to be amplified, and the other complementary to the (−)-strand at the other end. Because the newly-synthesized DNA strands can subsequently serve as additional templates for the same primer sequences, successive rounds of primer annealing, strand elongation, and dissociation may produce rapid and highly-specific amplification of the desired sequence. PCR also may be used to detect the existence of a defined sequence in a DNA sample. In a preferred embodiment of the present invention, the hybridization products are mixed with suitable PCR reagents. A PCR reaction is then performed, to amplify the hybridization products.

In a preferred embodiment, the sequencing library is constructed using the virome capture sequencing platform in a cleavable array. Nucleic acids from the sample are extracted and subjected to reverse transcriptase treatment and ligated to an adaptor comprising an identifier and sequences for priming for amplification. The oligonucleotides comprising the sequence capture platform are synthesized using a cleavable array platform wherein the oligonucleotides are biotinylated. The biotinylated oligonucleotides are then cleaved from the solid matrix into solution with the nucleic acids from the sample to enable hybridization of the oligonucleotides comprising the capture sequence platform to any viral nucleic acids in solution. After hybridization, nucleic acid(s) from the sample bound to the biotinylated oligonucleotides comprising the sequence capture platform, i.e., hybridization product(s), are collected by streptavidin magnetic beads, and amplified by PCR using the adaptor sequences as specific priming sites, resulting in an amplified product for sequencing on any known HTS systems (Ion, Illumina, 454) and any HTS system developed in the future.

In a further embodiment, the sequencing library can be directly sequenced using any method known in the art. In other words, the nucleic acids captured by the platform can be sequenced without amplification.

Methods and Systems for Simultaneous Detection, Identification, and/or Characterization of All Viruses Known or Suspected to Infect Vertebrates The present invention includes methods and systems for the simultaneous detection of the of all viruses known or suspected to infect vertebrates in any sample, the determination and characterization of viruses present in any sample, and the identification of novel viruses in any sample utilizing the novel virome capture sequencing platform.

The methods and systems of the present invention may be used to detect viruses, known and novel, in research, clinical, environmental, and food samples. Additional applications include, without limitation, detection of infectious pathogens, the screening of blood products (e.g., screening blood products for infectious agents), biodefense, food safety, environmental contamination, forensics, and genetic-comparability studies. The present invention also provides methods and systems for detecting viruses in cells, cell culture, cell culture medium and other compositions used for the development of pharmaceutical and therapeutic agents. Accordingly, the present invention provides methods and systems for a myriad of specific applications, including, without limitation, a method for determining the presence of viruses and viral nucleic acid sequence in a sample, a method for screening blood products, a method for assaying a food product for contamination, a method for assaying a sample for environmental contamination, and a method for detecting genetically-modified organisms. The present invention further provides use of the system in such general applications as biodefense against bio-terrorism, forensics, and genetic-comparability studies.

The subject may be any animal, particularly a vertebrate and more particularly a mammal, including, without limitation, a cow, dog, human, monkey, mouse, pig, or rat. Preferably, the subject is a human. The subject may be known to have a pathogen infection, suspected of having a pathogen infection, or believed not to have a pathogen infection.

The systems and methods described herein support the multiplex detection of multiple viruses and viral transcripts in any sample.

Thus one embodiment of the present invention provides a system for the simultaneous detection of all viruses known or suspected to infect vertebrates in any sample. The system includes at least one subsystem wherein the subsystem includes a virome capture sequencing platform as described herein. The system can also include additional subsystems for the purpose of: isolation and preparation of the nucleic acid fragments from the sample; hybridization of the nucleic acid fragments from the sample with the oligonucleotides of the virome capture sequencing platform to form hybridization product(s); amplification of the hybridization product(s); and sequencing the hybridization product(s).

The present invention also provides a system for the simultaneous determination and characterization of all viruses known to infect vertebrates in any sample. The system includes at least one subsystem wherein the subsystem includes a virome capture sequencing platform as described herein. The system can also include additional subsystems for the purpose of: isolation and preparation of the nucleic acid fragments from the sample; hybridization of the nucleic acid fragments from the sample with the oligonucleotides of the virome capture sequencing platform to form hybridization product(s); amplification of the hybridization product(s); sequencing the hybridization product(s); and identification and characterization of the virus by the comparison between the sequences of the hybridization products and the known viruses.

The present invention also provides a system for the identification of novel viruses in any sample. The system includes at least one subsystem wherein the subsystem includes a virome capture sequencing platform as described herein. The system can also include additional subsystems for the purpose of: isolation and preparation of the nucleic acid fragments from the sample; hybridization of the nucleic acid fragments from the sample with the oligonucleotides of the virome capture sequencing platform to form hybridization product(s); amplification of the hybridization product(s); sequencing the hybridization product(s); and identifying the virus as novel by the comparison between the sequences of the hybridization products and the known viruses.

Additionally, the present invention provides a method for the simultaneous detection of all viruses known or suspected to infect vertebrates in any sample, including the steps of: obtaining the sample; isolating and preparing the nucleic acid fragments from the sample; contacting the nucleic acid fragments from the sample with the oligonucleotides of virome capture sequencing platform under conditions sufficient for the nucleic acid fragments and the oligonucleotides of the virome capture sequencing platform to hybridize; and detecting any hybridization products formed between the nucleic acid fragments and the oligonucleotides of the virome capture sequencing platform.

This method can also include a step to amplify and sequence the hybridization products The present invention provides a method for the simultaneous determination and characterization of all viruses known or suspected to infect vertebrates in any sample, including the steps of: obtaining the sample; isolating and preparing the nucleic acid fragments from the sample;

contacting the nucleic acid fragments from the sample with the oligonucleotides of the virome capture sequencing platform under conditions sufficient for the nucleic acid fragments and the oligonucleotides of the virome capture sequencing platform to hybridize; sequencing any hybridization products formed between the nucleic acid fragments and the oligonucleotides of the virome capture sequencing platform; comparing the sequences of the hybridization product(s) with sequence of known viruses; and determining and characterizing the virus in the sample by the comparison of the sequences of the hybridization product(s) with sequence of known viruses.

This method can also include a step to amplify the hybridization products.

The present invention provides a method for the detecting the presence of novel viruses in any sample, including the steps of: obtaining the sample; isolating and preparing the nucleic acid fragments from the sample; contacting the nucleic acid fragments from the sample with the oligonucleotides of virome capture sequencing platform under conditions sufficient for the nucleic acid fragments and the oligonucleotides of the virome capture sequencing platform to hybridize; sequencing any hybridization products formed between the nucleic acid fragments and the virome capture sequencing platform; comparing the sequences of the hybridization product(s) with sequence of known viruses; and determining and characterizing the virus in the sample by the comparison of the sequences of the hybridization product(s) with sequence of known viruses.

This method can also include a step to amplify the hybridization products.

When practicing the methods for the determination and characterization of viruses in a sample and methods of detecting the presence of a novel virus in a sample, the sequence(s) of the hybridization products are compared to the nucleic acid sequences of known viruses. This can be done using databases in the form of a variety of media for their use.

As disclosed above, the methods of the present invention for the simultaneous detection, identification and/or characterization of all viruses known or suspected to infect vertebrates can be performed on any sample suspected of having viruses or viral nucleic acids, including but not limited to biological samples, environmental samples, or food samples. A preferred sample is a biological sample. A biological sample may be obtained from a tissue of a subject or bodily fluid from a subject including but not limited to nasopharyngeal aspirate, blood, cerebrospinal fluid, saliva, serum, urine, sputum, bronchial lavage, pericardial fluid, or peritoneal fluid, or a solid such as feces. A biological sample can also be cells, cell culture or cell culture medium. The sample may or may not comprise or contain any viral nucleic acids.

In a preferred embodiment, the sample is from a vertebrate subject, and in a most preferred embodiment, the sample is from a human subject. In another preferred embodiment, the sample comprises blood and is being tested prior to transfusion. In another preferred embodiment, the sample comprises cells, cell culture, cell culture medium or any other composition being used for developing pharmaceutical and therapeutic agents.

Kits

The invention also includes reagents and kits for practicing the methods of the invention. These reagents and kits may vary.

One reagent would be the virome capture sequencing platform. The platform could be in the form of a collection of oligonucleotide probes which comprise sequences derived from the genome of all of the viruses that are known or suspected to infect vertebrates. This collection of oligonucleotide probes, i.e., a library, can be in solution or attached to a solid state. Additionally, the oligonucleotide probes can be modified for use in a reaction. A preferred modification is the addition of biotin to the probes.

The platform can also be in the form of a searchable database with information regarding the oligonucleotides including at least sequence information, length and melting temperature, and the viral origin.

Other reagents in the kit could include reagents for isolating and preparing nucleic acids from a sample, hybridizing the nucleic acid fragments from the sample with the oligonucleotides of the platform, amplifying the hybridization products, and obtaining sequence information.

Kits of the subject invention may include any of the above-mentioned reagents, as well as reference/control sequences that can be used to compare the test sequence information obtained, by for example, suitable computing means based upon an input of sequence information.

In addition, kits would also further include instructions.

A further embodiment is a kit for designing and/or constructing the virome capture sequencing platform comprising analytical tools to choose viral sequence information and break the coding sequences into fragments for oligonucleotides with the proper parameters for the platform including proper length, melting temperature, GC distribution, distance spaced between the oligonucleotides on the coding sequences, and percentage sequence identity. This kit could also include instructions as to database and coding sequence choice.

EXAMPLES

The present invention may be better understood by reference to the following non-limiting examples, which are presented in order to more fully illustrate the preferred embodiments of the invention. They should in no way be construed to limit the broad scope of the invention.

Example 1

Materials and Methods Used for Examples 2-6
Samples and Specimens

Facsimiles of clinical specimens were generated in a background of nucleic acids (NA) extracted from normal human lung tissue, EDTA-blood or serum. The samples were spiked with viral NA and quantitated by virus-specific TaqMan real time (reverse transcription)-polymerase chain reaction (qPCR). NA from cell culture, blood, serum or tissue samples was extracted using the easyMAG system (bioMerieux, Marcyl l'Etoile, France) or AllPrep DNA/RNA kits (Qiagen, Hilden, Germany). Background NA was quantitated by Nanodrop (Wilmington, Del., USA) or Bioanalyzer 2100 (Agilent, Santa Clara, Calif., USA) and mixed with variable quantities of viral NA derived from enterovirus D68 (EV234 D68, (Mercer et al. 2014), West Nile virus (WNV, (Clark et al. 2015)), dengue virus 3 (DENV-3, (Bent et al. 2013)) and Middle East Respiratory Syndrome coronavirus (MERS-CoV; (Depledge et al. 2011)), representing single strand, positive sense RNA viruses of differing genome size; Ebola virus (EBOV) influenza A virus H3N2 (FLUAV, A/Moscow/10/99, WHO Influenza Centre, MRC, London, GB) and Cache Valley virus (CVV, (Brown et al. 2014), representing non-segmented and segmented negative strand RNA viruses; and herpes simplex virus 1 (HHV-1, ATCC VR-733), as a large double strand DNA virus. Spiking was performed using NA stocks banked at the Center of Infection and Immunity originally derived from virus culture or positive diagnostic specimens, with the exception of EBOV, which was provided as non-infectious nucleic acid extract by Peter Jahrling at the National Institute of Allergy and Infectious Diseases, National Institutes of Health. TaqMan PCR primer and probes for the various viruses are cited or available on request.

To determine the limit of detection and to assess VirCapSeq-VERT in comparison to conventional target enrichment procedures, normal human lung tissue homogenate, EDTA-blood, or serum samples were spiked with different amounts of EV-D68, HHV-1 and FLUAV live virus stock quantitated by qPCR.

Clinical samples included a human nasal swab sample known to be positive for EV-D68 (Tokarz et al. 2012); liver specimens from deer mice infected with deer mouse hepacivirus (Kapoor et al. 2013); a sample of bat feces pellets in which rotaviral sequences had been identified (unpublished); and serum samples from hemophilia patients co-infected with hepatitis C virus (HCV), GB virus C (GBV-C), human immunodeficiency virus (HIV) and torque teno virus (TTV).

Selection of Probe Sequences

The EMBL Coding Domain Sequence database (release 122, December 2014;), containing 2,199,467 records was clustered at 96% sequence identity by CD-Hit (Li and Godzik 2006), yielding a database of 401,716 representative sequences spanning all virus sequence records, excluding bacteriophages. A list of all virus genera known to infect vertebrates was generated from the Master Species List of the International Committee on Taxonomy of Viruses. Through cross-referencing protein IDs with NCBI Taxonomy IDs, a set of 342,438 coding sequence records was identified for the selected virus genera. The sequences were broken into fragments, clustered at 90% sequence identity and used to generate 100 nt probe sequences that were tiled across the genes at approximately 25-50 nt intervals. A library of 1,993,200 oligonucleotide probes was selected. The NimbleGen cleavable array platform was employed for synthesis of the biotinylated, soluble probe library (SeqCap EZ Choice; Roche/NimbleGen, Basel, Switzerland), and probe sequences were refined by adjusting their lengths to conform to NimbleGen synthesis parameters such as maximum $T_m$ or homopolymer repeat length.

Conventional Target Sequence Enrichment Procedures

Conventional virus enrichment methods commonly used in metagenomic sequencing-based virus discovery include filtration and pre-extraction nuclease treatments often combined with post-extraction DNase I and/or depletion of ribosomal rRNA sequences. Briefly, samples (100-300 µl) were filtered through 0.45 µm pore-size sterile disk filters (Merck/Millipore, Billerica, Mass., USA) to enrich for viruses over cells or bacteria. The flow-through was treated with 1 µl RNase A (10 mg/ml; Thermo Fisher, Waltham, Mass., USA) for 15 minutes at room temperature, followed by a cocktail of 8 U Turbo DNase (Thermo Fisher), 250 U Benzonase (Merck/Millipore) and 10 mM $MgCl_2$ for 45 minutes at room temperature to digest non-particle-protected NAs. Protected NAs such as in viral particles were extracted by easyMAG (bioMerieux) or AllPrep kits (Qiagen). Post-extraction digestion by DNase I (2 U/µg DNA for 15 minutes at 37° C.; Thermo Fisher) was added in some instances to digest chromosomal DNA (cellar, bacterial), but will also digest viral DNA (e.g. HHV-1 DNA, whereas mRNA transcripts generated from actively replicating cellular virus would be maintained). Depletion of non-desired host mRNA sequences was achieved using RiboZero Magnetic Kits (Illumina, San Diego, Calif., USA). Enriched preparations were subjected to reverse transcription and sequence library preparation.

Conventional HTS

Total NA extracts were reverse transcribed using SuperScript III (Thermo Fisher) with random hexamers. The cDNA was RNase-H treated prior to second strand synthesis with Klenow Fragment (New England Biolabs, Ipswich, Mass., USA). The generated double stranded cDNA was sheared to an average fragment size of 200 base pairs using manufacturer's standard settings (Covaris focused-ultrasonicator E210; Woburn, Mass., USA). Sheared product was purified (AxyPrep Mag PCR Clean-Up beads; Axygen/Corning, Corning, N.Y., USA) and libraries constructed using KAPA Library Preparation kits (KAPA, Wilmington, Mass., USA). For NA input quantities of 10-100 ng double stranded cDNA, the cycle number of the final PCR amplification was increased to 12 cycles, instead of 9 cycles for sample >100 ng double stranded cDNA. Final products were purified (AxyPrep) and quantitated by Bioanalyzer (Agilent) for Illumina sequencing.

Virome Capture Sequencing

Libraries were prepared following essentially the standard KAPA protocol but including viral sequence capture, following mainly the SeqCap RNA Enrichment System protocol (www.nimblegen.com/products/lit/07279337001_RNG_SeqCapRNA303UGuide_v1p0.pdf).

Briefly, total NA extract was reverse transcribed using SuperScript III (Thermo Fisher) with random hexamers. The cDNA was RNase-H treated prior to second strand synthesis with Klenow Fragment (New England Biolabs). The resulting double stranded cDNA/DNA mix was sheared to an average fragment size of 200 base pairs using manufacturer's standard settings (Covaris focused-ultrasonicator E210). Sheared product was purified (AxyPrep) and libraries constructed using KAPA Library Preparation kits (KAPA) with rs/NimbleGen Adapter kits. Quality and quantity of libraries were checked using Bioanalyzer (Agilent). The libraries were then mixed with SeqCap HE Universal Oligo, SeqCap HE index oligos and COT DNA and vacuum evaporated at 60° C. for approximately 40 minutes. Dried samples were mixed with 2× hybridization buffer and Hybridization Component A (Roche/NimbleGen) prior to denaturation at 95° C. for 10 minutes. 4.5 µl of VirCap probe library was added and hybridized at 47° C. for 12 hours in a standard PCR thermocycler. SeqCap Pure Capture Beads (Roche/NimbleGen) were washed two times, then mixed with the hybridization mix and kept at 47° C. for 45 minutes with vortexing every 10-15 minutes for 10 seconds. The streptavidin-capture beads complexed with biotinylated VirCapSeq-VERT probes were trapped (DynaMag-2 magnet, Thermo Fisher) and washed once at 47° C. and then two more times at room temperature with wash buffers of increasing stringency. Finally, beads were suspended in 50 µl water and directly subjected to post-hybridization PCR (SeqCap EZ Accessory Kit V2, Roche/NimbleGen). The PCR products were purified (Agencourt Ampure DNA purification beads, Beckman Coulter, Brea, Calif., USA) and quantitated by Bioanalyzer (Agilent) for Illumina sequencing.

Data Analysis and Bioinformatics Pipeline

Sequencing on the Illumina HiSeq 2500 platform (Illumina) resulted in an average of 210 million reads per lane. Samples were demultiplexed using Illumina software and FastQ files were generated. Demultiplexed and Q30 filtered FastQ files were mapped against reference genomes from GenBank with Bowtie2 mapper 2.0.6. SAMtools (v 0.1.19; (Li et al. 2006)) were used to generate the consensus genomes and coverage statistics. Integrative Genomics Viewer (v 2.3.55; (Robinson et al. 2011)) was used to generate coverage plots. Host background levels were determined from Bowtie2 mappings against the host genomes downloaded from NCBI. Sequencing data obtained from the unknown samples was preprocessed using PRINSEQ (v 0.20.2; (Schmieder and Edwards 2011)) software and filtered reads were aligned against the host reference databases to remove the host background. The host subtracted reads were de novo assembled using MIRA (v 4.0; (Chevreux et al. 1999)) or SOAPdenovo2 (v 2.04: (Luo et al. 2012)) assemblers and contigs and unique singletons were subjected to homology search using MegaBlast against the GenBank nucleotide database; sequences that showed poor or no homology at the nucleotide level were screened by Blastx against the viral GenBank protein database. Viral sequences from Blastx analysis were subjected to another round of Blastx homology search against the entire GenBank protein database to correct for biased e-values and taxonomic misassignments. Based on the contigs identified for different viral strains, GenBank sequences were downloaded and used for mapping the whole dataset to recover partial or complete genomes. Viral read numbers were obtained from counting number of reads mapping to contig sequences and unassembled singeltons and percentages calculated in relation to the total read number obtained. Percentages were converted into heatmaps using MultiExperiment Viewer (MeV v4.9, (Saeed et al. 2003)).

Example 2

Probe Design Strategy

The objective was to target all known viruses that can infect animals, including humans. Toward this end, oligonucleotides were selected to represent all viral taxa containing at least one virus known to infect vertebrates; virus families that include exclusively viruses infecting plants or insects were excluded (Table 1). Coding sequences were extracted from the EMBL Coding Domain Sequence database, clustered at 96% sequence identity and used to select 100-mer oligonucleotides spaced by approximately 25 to 50 nucleotides (nt) along each sequence. To address sequence variation, oligonucleotide mutant or variant sequences were retained if sequences diverged by more than 10%. Where technical complexity in oligonucleotide synthesis was challenging due to $T_m$ or homopolymer repeats, probe sequences were refined by shortening and adjusting their start/stop positions. The final library comprised 1,993,176 oligonucleotides ranging in length from 50 to 100 nt, with a mean length of 74.3 and a median length of 74 with a $T_m$ ranging from 58.7° C. to 101° C., with a mean $T_m$ of 79.69° C. and median $T_m$ of 79.1° C.

Figure 1B:
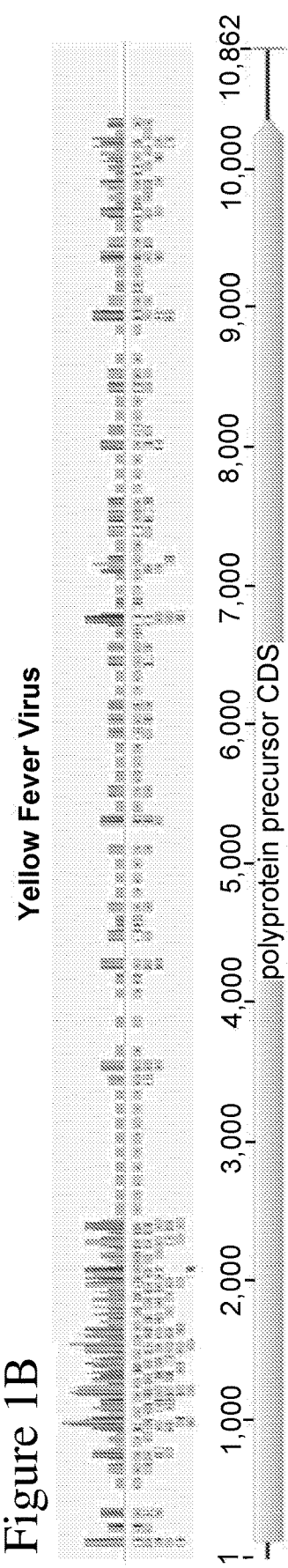
Figure 1C:
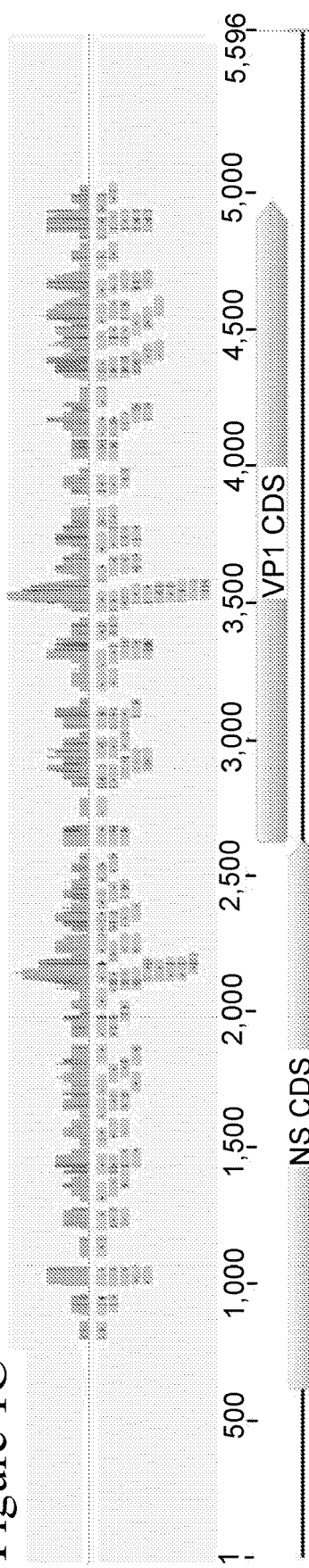

The selected probe library was evaluated in silico to determine whether it provided uniform coverage of the targeted virus sequences. The analysis indicated that probe numbers were proportional to the amount of available sequence information, resulting in a 88-98% estimated coverage of target sequences when assuming an 'outreach' for each probe of approximately 100 nt to either side (Table 2). The probe library was mapped against a database of 100 reference virus genome sequences representing double/single stranded DNA and RNA, positive/negative RNA, circular, linear and segmented viruses, using a minimum nt identity of 90%. The probe library covered targeted genome sequences with probes spaced at <150 nt intervals (FIG. 1) but provided no coverage of non-coding regions (e.g. poliovirus 5'-UTR, FIG. 1A). Highest probe coverage was evident in divergent genome regions (e.g. yellow fever virus' E gene region; approximately position 1000-2500, FIG. 1B). In silico analysis indicated that the VirCapSeq-VERT probe library included oligonucleotides that selectively hybridize to genomes of vertebrate viruses but not to those of bacteriophages, plant or fungal viruses.

TABLE 1

| Virus Taxa Selected for VirCapSeq-VERT Probe Design | | | |
|---|---|---|---|
| Name | tax_id | ParentName | parent tax_id |
| Adenoviridae | 10508 | dsDNA viruses, no RNA stage | 35237 |
| Alloherpesviridae | 548682 | Herpesvirales | 548681 |
| *Alphacoronavirus* | 693996 | Coronavirinae | 693995 |
| Alphaherpesvirinae | 10293 | Herpesviridae | 10292 |
| *Alphanodavirus* | 143920 | Nodaviridae | 12283 |
| *Alphapapillomavirus* | 333750 | Papillomaviridae | 151340 |
| *Alphapermutotetravirus* | 1283211 | Permutotetraviridae | 1283210 |
| *Alpharetrovirus* | 153057 | Orthoretrovirinae | 327045 |
| *Alphatorquevirus* | 687331 | Anelloviridae | 687329 |
| *Alphavirus* | 11019 | Togaviridae | 11018 |
| *Amdoparvovirus* | 310911 | Parvovirinae | 40119 |
| Anelloviridae | 687329 | ssDNA viruses | 29258 |
| *Aphthovirus* | 12109 | Picornaviridae | 12058 |
| *Aquabirnavirus* | 39750 | Birnaviridae | 10993 |
| *Aquamavirus* | 1330065 | Picornaviridae | 12058 |
| *Aquaparamyxovirus* | 1232658 | Paramyxovirinae | 11159 |
| *Aquareovirus* | 10979 | Spinareovirinae | 689831 |
| Arenaviridae | 11617 | ssRNA negative-strand viruses | 35301 |
| *Arenavirus* | 11618 | Arenaviridae | 11617 |
| Arteriviridae | 76803 | Nidovirales | 76804 |
| *Arterivirus* | 11046 | Arteriviridae | 76803 |
| Asfarviridae | 137992 | dsDNA viruses, no RNA stage | 35237 |
| *Asfivirus* | 39743 | Asfarviridae | 137992 |
| Astroviridae | 39733 | ssRNA positive-strand viruses, no DNA stage | 35278 |

TABLE 1-continued

Virus Taxa Selected for VirCapSeq-VERT Probe Design

| Name | tax_id | ParentName | parent tax_id |
|---|---|---|---|
| *Atadenovirus* | 100953 | Adenoviridae | 10508 |
| *Aurivirus* | 1513230 | Malacoherpesviridae | 548685 |
| *Avastrovirus* | 249589 | Astroviridae | 39733 |
| *Aveparvovirus* | 1511864 | Parvovirinae | 40119 |
| *Aviadenovirus* | 10552 | Adenoviridae | 10508 |
| *Avibirnavirus* | 39751 | Birnaviridae | 10993 |
| *Avihepadnavirus* | 10437 | Hepadnaviridae | 10404 |
| *Avihepatovirus* | 691955 | Picornaviridae | 12058 |
| *Avipoxvirus* | 10260 | Chordopoxvirinae | 10241 |
| *Avisivirus* | 1511771 | Picornaviridae | 12058 |
| *Avulavirus* | 260963 | Paramyxovirinae | 11159 |
| *Bafinivirus* | 694018 | Torovirinae | 694017 |
| *Batrachovirus* | 692605 | Alloherpesviridae | 548682 |
| *Betacoronavirus* | 694002 | Coronavirinae | 693995 |
| Betaherpesvirinae | 10357 | Herpesviridae | 10292 |
| *Betanodavirus* | 143919 | Nodaviridae | 12283 |
| *Betapapillomavirus* | 333922 | Papillomaviridae | 151340 |
| *Betaretrovirus* | 140052 | Orthoretrovirinae | 327045 |
| *Betatorquevirus* | 687332 | Anelloviridae | 687329 |
| Birnaviridae | 10993 | dsRNA viruses | 35325 |
| *Blosnavirus* | 564643 | Birnaviridae | 10993 |
| *Bocaparvovirus* | 1507401 | Parvovirinae | 40119 |
| Bornaviridae | 178830 | Mononegavirales | 11157 |
| *Bornavirus* | 186458 | Bornaviridae | 178830 |
| *Bracorhabdovirus* | 490109 | unclassified Rhabdoviridae | 35303 |
| Bunyaviridae | 11571 | ssRNA negative-strand viruses | 35301 |
| Caliciviridae | 11974 | ssRNA positive-strand viruses, no DNA stage | 35278 |
| *Capripoxvirus* | 10265 | Chordopoxvirinae | 10241 |
| *Cardiovirus* | 12103 | Picornaviridae | 12058 |
| *Cervidpoxvirus* | 573055 | Chordopoxvirinae | 10241 |
| *Chipapillomavirus* | 934800 | Papillomaviridae | 151340 |
| *Chloriridovirus* | 10491 | Iridoviridae | 10486 |
| Chordopoxvirinae | 10241 | Poxviridae | 10240 |
| Circoviridae | 39724 | ssDNA viruses | 29258 |
| *Circovirus* | 39725 | Circoviridae | 39724 |
| *Coltivirus* | 10911 | Spinareovirinae | 689831 |
| *Copiparvovirus* | 1511888 | Parvovirinae | 40119 |
| Coronaviridae | 11118 | Nidovirales | 76804 |
| Coronavirinae | 693995 | Coronaviridae | 11118 |
| *Cosavirus* | 586418 | Picornaviridae | 12058 |
| *Crocodylidpoxvirus* | 1285599 | Chordopoxvirinae | 10241 |
| *Cuevavirus* | 1513236 | Filoviridae | 11266 |
| *Cyprinivirus* | 692606 | Alloherpesviridae | 548682 |
| *Cytomegalovirus* | 10358 | Betaherpesvirinae | 10357 |
| *Cytorhabdovirus* | 11305 | Rhabdoviridae | 11270 |
| *Deltacoronavirus* | 1159901 | Coronavirinae | 693995 |
| *Deltapapillomavirus* | 325454 | Papillomaviridae | 151340 |
| *Deltaretrovirus* | 153136 | Orthoretrovirinae | 327045 |
| *Deltatorquevirus* | 687334 | Anelloviridae | 687329 |
| *Deltavirus* | 39759 | Viruses | 10239 |
| Dengue virus group | 11052 | Flavivirus | 11051 |
| Densovirinae | 40120 | Parvoviridae | 10780 |
| *Dependoparvovirus* | 10803 | Parvovirinae | 40119 |
| *Dicipivirus* | 1330067 | Picornaviridae | 12058 |
| *Dinornavirus* | 674976 | Alvernaviridae | 866787 |
| *Dyodeltapapillomavirus* | 936056 | Papillomaviridae | 151340 |
| *Dyoepsilonpapillomavirus* | 935646 | Papillomaviridae | 151340 |
| *Dyoetapapillomavirus* | 935641 | Papillomaviridae | 151340 |
| *Dyoiotapapillomavirus* | 934804 | Papillomaviridae | 151340 |
| *Dyokappapapillomavirus* | 1513238 | Papillomaviridae | 151340 |
| *Dyolambdapapillomavirus* | 1513239 | Papillomaviridae | 151340 |
| *Dyomupapillomavirus* | 1513240 | Papillomaviridae | 151340 |
| *Dyonupapillomavirus* | 1513241 | Papillomaviridae | 151340 |
| *Dyoomikronpapillomavirus* | 1513242 | Papillomaviridae | 151340 |
| *Dyopipapillomavirus* | 1513243 | Papillomaviridae | 151340 |
| *Dyorhopapillomavirus* | 1513244 | Papillomaviridae | 151340 |
| *Dyosigmapapillomavirus* | 1513245 | Papillomaviridae | 151340 |
| *Dyothetapapillomavirus* | 1052159 | Papillomaviridae | 151340 |
| *Dyoxipapillomavirus* | 1513246 | Papillomaviridae | 151340 |
| *Dyozetapapillomavirus* | 934803 | Papillomaviridae | 151340 |
| *Ebolavirus* | 186536 | Filoviridae | 11266 |
| *Enterovirus* | 12059 | Picornaviridae | 12058 |
| Entomopoxvirinae | 10284 | Poxviridae | 10240 |
| *Ephemerovirus* | 32613 | Rhabdoviridae | 11270 |

TABLE 1-continued

Virus Taxa Selected for VirCapSeq-VERT Probe Design

| Name | tax_id | ParentName | parent tax_id |
|---|---|---|---|
| *Epsilonretrovirus* | 153137 | Orthoretrovirinae | 327045 |
| *Epsilontorquevirus* | 687335 | Anelloviridae | 687329 |
| Equine lentivirus group | 11654 | *Lentivirus* | 11646 |
| *Erbovirus* | 194961 | Picornaviridae | 12058 |
| *Erythroparvovirus* | 40121 | Parvovirinae | 40119 |
| *Etapapillomavirus* | 325458 | Papillomaviridae | 151340 |
| *Etatorquevirus* | 687337 | Anelloviridae | 687329 |
| *Ferlavirus* | 1283308 | Paramyxovirinae | 11159 |
| Filoviridae | 11266 | Mononegavirales | 11157 |
| Flaviviridae | 11050 | ssRNA positive-strand viruses, no DNA stage | 35278 |
| *Flavivirus* | 11051 | Flaviviridae | 11050 |
| *Gallivirus* | 1511775 | Picornaviridae | 12058 |
| *Gammacoronavirus* | 694013 | Coronavirinae | 693995 |
| Gammaherpesvirinae | 10374 | Herpesviridae | 10292 |
| *Gammapapillomavirus* | 325455 | Papillomaviridae | 151340 |
| *Gammaretrovirus* | 153135 | Orthoretrovirinae | 327045 |
| *Gammatorquevirus* | 687333 | Anelloviridae | 687329 |
| *Gyrovirus* | 227307 | Circoviridae | 39724 |
| *Hantavirus* | 11598 | Bunyaviridae | 11571 |
| *Henipavirus* | 260964 | Paramyxovirinae | 11159 |
| *Hepacivirus* | 11102 | Flaviviridae | 11050 |
| Hepadnaviridae | 10404 | Retro-transcribing viruses | 35268 |
| *Hepatovirus* | 12091 | Picornaviridae | 12058 |
| Hepeviridae | 291484 | ssRNA positive-strand viruses, no DNA stage | 35278 |
| *Hepevirus* | 186677 | Hepeviridae | 291484 |
| *Herpesvirales* | 548681 | dsDNA viruses, no RNA stage | 35237 |
| Herpesviridae | 10292 | Herpesvirales | 548681 |
| *Hunnivirus* | 1431456 | Picornaviridae | 12058 |
| *Ichtadenovirus* | 691957 | Adenoviridae | 10508 |
| *Ictalurivirus* | 172653 | Alloherpesviridae | 548682 |
| *Iltovirus* | 180255 | Alphaherpesvirinae | 10293 |
| Influenzavirus D | 1511083 | unclassified Orthomyxoviridae | 35324 |
| Intracisternal A-particles | 11749 | unclassified Retroviridae | 35276 |
| *Iotatorquevirus* | 687339 | Anelloviridae | 687329 |
| Iridoviridae | 10486 | dsDNA viruses, no RNA stage | 35237 |
| *Iridovirus* | 10487 | Iridoviridae | 10486 |
| *Isavirus* | 324913 | Orthomyxoviridae | 11308 |
| Japanese encephalitis virus group | 11071 | *Flavivirus* | 11051 |
| *Kappapapillomavirus* | 325457 | Papillomaviridae | 151340 |
| *Kappatorquevirus* | 1218487 | Anelloviridae | 687329 |
| *Kobuvirus* | 194960 | Picornaviridae | 12058 |
| Kokobera virus group | 303179 | *Flavivirus* | 11051 |
| *Lagovirus* | 95339 | Caliciviridae | 11974 |
| *Lambdapapillomavirus* | 325462 | Papillomaviridae | 151340 |
| *Lambdatorquevirus* | 1218489 | Anelloviridae | 687329 |
| *Lentivirus* | 11646 | Orthoretrovirinae | 327045 |
| *Leporipoxvirus* | 10270 | Chordopoxvirinae | 10241 |
| *Lymphocryptovirus* | 10375 | Gammaherpesvirinae | 10374 |
| *Lymphocystivirus* | 10494 | Iridoviridae | 10486 |
| *Lyssavirus* | 11286 | Rhabdoviridae | 11270 |
| *Macavirus* | 548687 | Gammaherpesvirinae | 10374 |
| Malacoherpesviridae | 548685 | Herpesvirales | 548681 |
| *Mamastrovirus* | 249588 | Astroviridae | 39733 |
| *Marburgvirus* | 186537 | Filoviridae | 11266 |
| *Mardivirus* | 180252 | Alphaherpesvirinae | 10293 |
| *Mastadenovirus* | 10509 | Adenoviridae | 10508 |
| *Megalocytivirus* | 308906 | Iridoviridae | 10486 |
| *Megrivirus* | 1330069 | Picornaviridae | 12058 |
| *Metapneumovirus* | 162387 | Pneumovirinae | 11244 |
| *Mischivirus* | 1511778 | Picornaviridae | 12058 |
| Modoc virus group | 29260 | *Flavivirus* | 11051 |
| *Molluscipoxvirus* | 10278 | Chordopoxvirinae | 10241 |
| Mononegavirales | 11157 | ssRNA negative-strand viruses | 35301 |
| *Morbillivirus* | 11229 | Paramyxovirinae | 11159 |
| *Mosavirus* | 1481451 | Picornaviridae | 12058 |
| mosquito-borne viruses | 59562 | *Flavivirus* | 11051 |
| *Mupapillomavirus* | 334202 | Papillomaviridae | 151340 |
| *Muromegalovirus* | 10365 | Betaherpesvirinae | 10357 |
| *Nairovirus* | 11592 | Bunyaviridae | 11571 |
| *Nebovirus* | 696855 | Caliciviridae | 11974 |
| *Negevirus* | 1307798 | unclassified ssRNA positive-strand viruses | 38173 |

TABLE 1-continued

Virus Taxa Selected for VirCapSeq-VERT Probe Design

| Name | tax_id | ParentName | parent tax_id |
|---|---|---|---|
| Nidovirales | 76804 | ssRNA positive-strand viruses, no DNA stage | 35278 |
| Nodaviridae | 12283 | ssRNA positive-strand viruses, no DNA stage | 35278 |
| *Norovirus* | 142786 | Caliciviridae | 11974 |
| *Novirhabdovirus* | 186778 | Rhabdoviridae | 11270 |
| Ntaya virus group | 29261 | *Flavivirus* | 11051 |
| *Nucleorhabdovirus* | 11306 | Rhabdoviridae | 11270 |
| *Nupapillomavirus* | 475861 | Papillomaviridae | 151340 |
| Nyamiviridae | 1513294 | Mononegavirales | 11157 |
| *Nyavirus* | 1513295 | Nyamiviridae | 1513294 |
| *Omegapapillomavirus* | 936061 | Papillomaviridae | 151340 |
| *Orbivirus* | 10892 | Sedoreovirinae | 689832 |
| *Orthobunyavirus* | 11572 | Bunyaviridae | 11571 |
| *Orthohepadnavirus* | 10405 | Hepadnaviridae | 10404 |
| Orthomyxoviridae | 11308 | ssRNA negative-strand viruses | 35301 |
| *Orthopoxvirus* | 10242 | Chordopoxvirinae | 10241 |
| *Orthoreovirus* | 10882 | Spinareovirinae | 689831 |
| Orthoretrovirinae | 327045 | Retroviridae | 11632 |
| *Oscivirus* | 1511780 | Picornaviridae | 12058 |
| *Ostreavirus* | 548686 | Malacoherpesviridae | 548685 |
| Papillomaviridae | 151340 | dsDNA viruses, no RNA stage | 35237 |
| Paramyxoviridae | 11158 | Mononegavirales | 11157 |
| Paramyxovirinae | 11159 | Paramyxoviridae | 11158 |
| *Parapoxvirus* | 10257 | Chordopoxvirinae | 10241 |
| *Parechovirus* | 138954 | Picornaviridae | 12058 |
| Parvoviridae | 10780 | ssDNA viruses | 29258 |
| Parvovirinae | 40119 | Parvoviridae | 10780 |
| *Pasivirus* | 1511782 | Picornaviridae | 12058 |
| *Passerivirus* | 1511802 | Picornaviridae | 12058 |
| *Pegivirus* | 1307799 | Flaviviridae | 11050 |
| *Percavirus* | 548688 | Gammaherpesvirinae | 10374 |
| *Perhabdovirus* | 1298653 | Rhabdoviridae | 11270 |
| *Pestivirus* | 11095 | Flaviviridae | 11050 |
| *Phipapillomavirus* | 934802 | Papillomaviridae | 151340 |
| *Phlebovirus* | 11584 | Bunyaviridae | 11571 |
| Picobirnaviridae | 585893 | dsRNA viruses | 35325 |
| *Picobirnavirus* | 104394 | Picobirnaviridae | 585893 |
| Picornavirales | 464095 | ssRNA positive-strand viruses, no DNA stage | 35278 |
| Picornaviridae | 12058 | Picornavirales | 464095 |
| *Pipapillomavirus* | 334211 | Papillomaviridae | 151340 |
| Pneumovirinae | 11244 | Paramyxoviridae | 11158 |
| *Pneumovirus* | 11245 | Pneumovirinae | 11244 |
| Polyomaviridae | 151341 | dsDNA viruses, no RNA stage | 35237 |
| *Polyomavirus* | 10624 | Polyomaviridae | 151341 |
| Poxviridae | 10240 | dsDNA viruses, no RNA stage | 35237 |
| *Proboscivirus* | 548689 | Betaherpesvirinae | 10357 |
| *Protoparvovirus* | 1506574 | Parvovirinae | 40119 |
| *Psipapillomavirus* | 935650 | Papillomaviridae | 151340 |
| *Quadrivirus* | 1299297 | Quadriviridae | 1299296 |
| *Quaranjavirus* | 1299308 | Orthomyxoviridae | 11308 |
| *Ranavirus* | 10492 | Iridoviridae | 10486 |
| *Recovirus* | 873551 | Caliciviridae | 11974 |
| Reoviridae | 10880 | dsRNA viruses | 35325 |
| *Respirovirus* | 186938 | Paramyxovirinae | 11159 |
| Retroviridae | 11632 | Retro-transcribing viruses | 35268 |
| Rhabdoviridae | 11270 | Mononegavirales | 11157 |
| *Rhadinovirus* | 10379 | Gammaherpesvirinae | 10374 |
| *Rhopapillomavirus* | 936057 | Papillomaviridae | 151340 |
| Rio Bravo virus group | 29262 | *Flavivirus* | 11051 |
| *Rosavirus* | 1511804 | Picornaviridae | 12058 |
| *Roseolovirus* | 40272 | Betaherpesvirinae | 10357 |
| *Rotavirus* | 10912 | Sedoreovirinae | 689832 |
| *Rubivirus* | 11040 | Togaviridae | 11018 |
| *Rubulavirus* | 39744 | Paramyxovirinae | 11159 |
| *Salivirus* | 688449 | Picornaviridae | 12058 |
| *Salmonivirus* | 692607 | Alloherpesviridae | 548682 |
| *Sapelovirus* | 686982 | Picornaviridae | 12058 |
| *Sapovirus* | 95341 | Caliciviridae | 11974 |
| *Scutavirus* | 1232637 | Alphaherpesvirinae | 10293 |
| Seaborne tick-borne virus group | 29264 | *Flavivirus* | 11051 |
| *Seadornavirus* | 208294 | Sedoreovirinae | 689832 |
| Sedoreovirinae | 689832 | Reoviridae | 10880 |

TABLE 1-continued

Virus Taxa Selected for VirCapSeq-VERT Probe Design

| Name | tax_id | ParentName | parent tax_id |
|---|---|---|---|
| *Senecavirus* | 586425 | Picornaviridae | 12058 |
| *Siadenovirus* | 129876 | Adenoviridae | 10508 |
| *Sigmapapillomavirus* | 935635 | Papillomaviridae | 151340 |
| *Sigmavirus* | 1308858 | Rhabdoviridae | 11270 |
| *Simplexvirus* | 10294 | Alphaherpesvirinae | 10293 |
| Spinareovirinae | 689831 | Reoviridae | 10880 |
| *Sprivivirus* | 1513299 | Rhabdoviridae | 11270 |
| Spumaretrovirinae | 327046 | Retroviridae | 11632 |
| *Spumavirus* | 11640 | Spumaretrovirinae | 327046 |
| *Suipoxvirus* | 10275 | Chordopoxvirinae | 10241 |
| *Taupapillomavirus* | 934799 | Papillomaviridae | 151340 |
| *Teschovirus* | 118139 | Picornaviridae | 12058 |
| *Tetraparvovirus* | 1511911 | Parvovirinae | 40119 |
| *Thetapapillomavirus* | 334213 | Papillomaviridae | 151340 |
| *Thetatorquevirus* | 687338 | Anelloviridae | 687329 |
| *Thogotovirus* | 35323 | Orthomyxoviridae | 11308 |
| *Tibrovirus* | 1299306 | Rhabdoviridae | 11270 |
| tick-borne encephalitis virus group | 29263 | *Flavivirus* | 11051 |
| Togaviridae | 11018 | ssRNA positive-strand viruses, no DNA stage | 35278 |
| Torovirinae | 694017 | Coronaviridae | 11118 |
| *Torovirus* | 11155 | Torovirinae | 694017 |
| *Tremovirus* | 689759 | Picornaviridae | 12058 |
| *Tupavirus* | 1513300 | Rhabdoviridae | 11270 |
| *Upsilonpapillomavirus* | 936058 | Papillomaviridae | 151340 |
| *Varicellovirus* | 10319 | Alphaherpesvirinae | 10293 |
| *Vesiculovirus* | 11271 | Rhabdoviridae | 11270 |
| *Vesivirus* | 95337 | Caliciviridae | 11974 |
| *Yatapoxvirus* | 10282 | Chordopoxvirinae | 10241 |
| Yellow fever virus group | 40005 | *Flavivirus* | 11051 |
| *Zetapapillomavirus* | 333918 | Papillomaviridae | 151340 |
| *Zetatorquevirus* | 687336 | Anelloviridae | 687329 |

TABLE 2

Probe Coverage for Selected Taxa

| Genome Organization | Family | Total CDS Sequences (96% Identity Clustering) | Megabases of Sequence Information | Taxonomic Groups * | Count of Probes (98% Blast Identity to Target) | Average Coverage per Gene (Probe + 100 nt Flank) |
|---|---|---|---|---|---|---|
| dsDNA viruses, no RNA stage | Adenoviridae | 3197 | 3.30 | 296 | 20669 | 94% |
| dsDNA viruses, no RNA stage | Asfarviridae | 504 | 0.40 | 5 | 2369 | 94% |
| dsDNA viruses, no RNA stage | Iridoviridae | 2632 | 2.48 | 67 | 16026 | 94% |
| dsDNA viruses, no RNA stage | Papillomaviridae | 2912 | 2.78 | 381 | 19363 | 95% |
| dsDNA viruses, no RNA stage | Polyomaviridae | 497 | 0.50 | 102 | 3097 | 95% |
| dsDNA viruses, no RNA stage | Poxviridae | 6863 | 6.50 | 143 | 38997 | 88% |
| dsDNA viruses, no RNA stage | Alloherpesviridae | 1054 | 1.60 | 17 | 11354 | 97% |
| dsDNA viruses, no RNA stage | Malacoherpesviridae | 162 | 0.24 | 3 | 1793 | 98% |
| dsDNA viruses, no RNA stage | Herpesviridae | 9420 | 12.25 | 491 | 79039 | 94% |
| ssDNA viruses | Anelloviridae | 1653 | 0.99 | 108 | 5914 | 93% |
| ssDNA viruses | Circoviridae | 765 | 0.53 | 141 | 2775 | 94% |
| ssDNA viruses | Parvoviridae | 1090 | 1.42 | 229 | 8944 | 95% |
| ssRNA circular | Deltavirus | 558 | 0.22 | 40 | 907 | 89% |
| dsRNA viruses | Picobirnaviridae | 228 | 0.13 | 62 | 860 | 96% |
| dsRNA viruses | Birnaviridae | 370 | 0.39 | 24 | 2285 | 95% |
| dsRNA viruses | Reoviridae | 6611 | 9.30 | 583 | 61406 | 96% |
| Retro-transcribing viruses | Hepadnaviridae | 3435 | 3.08 | 33 | 11747 | 97% |

TABLE 2-continued

Probe Coverage for Selected Taxa

| Genome Organization | Family | Total CDS Sequences (96% Identity Clustering) | Megabases of Sequence Information | Taxonomic Groups * | Count of Probes (98% Blast Identity to Target) | Average Coverage per Gene (Probe + 100 nt Flank) |
|---|---|---|---|---|---|---|
| Retro-transcribing viruses | Retroviridae | 214256 | 205.23 | 1569 | 790151 | 90% |
| ssRNA negative-strand viruses | Nyamiviridae | 23 | 0.05 | 4 | 315 | 96% |
| ssRNA negative-strand viruses | Bornaviridae | 178 | 0.19 | 13 | 1228 | 93% |
| ssRNA negative-strand viruses | Filoviridae | 92 | 0.18 | 14 | 1138 | 96% |
| ssRNA negative-strand viruses | Paramyxoviridae | 3531 | 4.21 | 310 | 23627 | 93% |
| ssRNA negative-strand viruses | Rhabdoviridae | 2210 | 3.20 | 217 | 20783 | 95% |
| ssRNA negative-strand viruses | Arenaviridae | 957 | 1.91 | 62 | 12403 | 94% |
| ssRNA negative-strand viruses | Bunyaviridae | 2875 | 5.63 | 535 | 39130 | 95% |
| ssRNA negative-strand viruses | Orthomyxoviridae | 8680 | 12.75 | 5231 | 64289 | 95% |
| ssRNA positive-strand viruses, no DNA stage | Arteriviridae | 3671 | 3.68 | 8 | 20024 | 95% |
| ssRNA positive-strand viruses, no DNA stage | Coronaviridae | 3436 | 6.90 | 389 | 41294 | 94% |
| ssRNA positive-strand viruses, no DNA stage | Picornaviridae | 13510 | 16.87 | 738 | 104910 | 94% |
| ssRNA positive-strand viruses, no DNA stage | Astroviridae | 1351 | 1.41 | 318 | 8959 | 95% |
| ssRNA positive-strand viruses, no DNA stage | Caliciviridae | 3924 | 3.83 | 2075 | 23064 | 90% |
| ssRNA positive-strand viruses, no DNA stage | Flaviviridae | 36921 | 46.72 | 391 | 222206 | 94% |
| ssRNA positive-strand viruses, no DNA stage | Hepeviridae | 2877 | 2.26 | 18 | 13489 | 92% |
| ssRNA positive-strand viruses, no DNA stage | Nodaviridae | 106 | 0.13 | 58 | 950 | 95% |
| ssRNA positive-strand viruses, no DNA stage | Togaviridae | 425 | 1.13 | 37 | 7415 | 96% |

* refers to the lowest NCBI taxID level

Example 3

Experimental Assessment of Efficiency

Figure 2A:
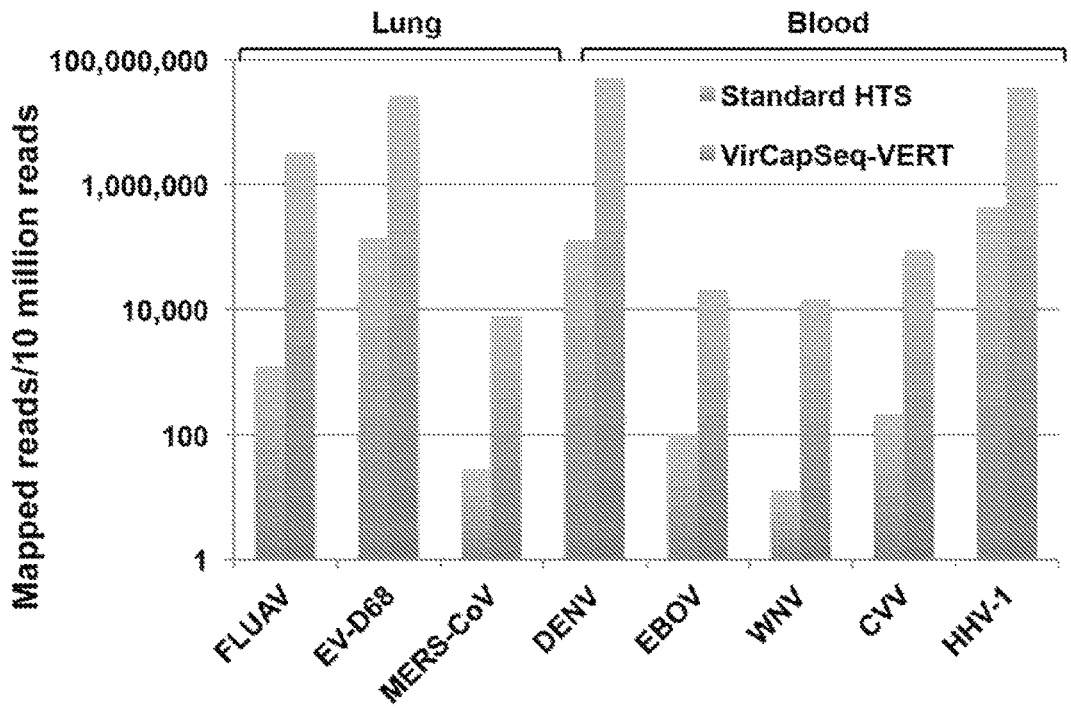
FIG. 2A shows the mapped reads per 10 million reads obtained by each method.
Figure 2B:
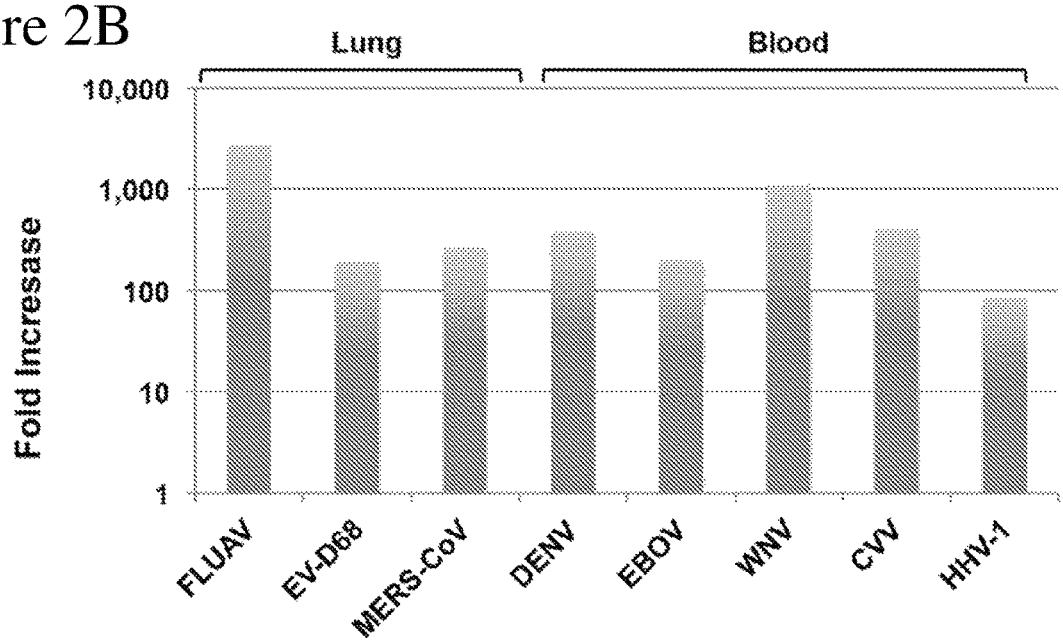
FIG. 2B shows the fold increase of mapped viral reads using VirCapSeq-VERT versus standard HTS. Abbreviations: FLUAV, influenza A virus; EVD-68, enterovirus D68; MERS-CoV, MERS coronavirus; DENV, dengue virus; EBOV, ebola virus; WNV, West Nile virus; CVV, Cache Valley virus; HHV-1, human herpesvirus-1.

Nucleic acid (NA) extracts of human lung tissue or whole blood were spiked with varying amounts of NAs representing large and small, positive and negative strand, segmented and non-segmented, as well as DNA and RNA viruses (Table 3). Spiked lung (pool 1) and blood (pool 2) NA preparations were divided and processed in parallel using a standard Illumina HTS protocol or the VirCapSeq-VERT system, whereby viral sequences are enriched by positive selection. Each of the preparations was sequenced on an Illumina HiSeq 2500 sequencer loading 2 lanes per sample. VirCapSeq-VERT resulted in a 100 to 1,000-fold increase in on-target (viral) reads and a reduction of host background reads from 99.7% to 68.2% in lung and from 99.4% to 38.5% in blood (FIG. 2). The average coverage also increased dramatically with nearly full-length sequence (>95%) obtained for all viruses (Table 4). FIG. 3 shows selected examples of sequence recovery for West Nile virus (WNV), Cache Valley virus (CVV), and Middle East Respiratory Syndrome coronavirus (MERS-CoV).

Figure 4:
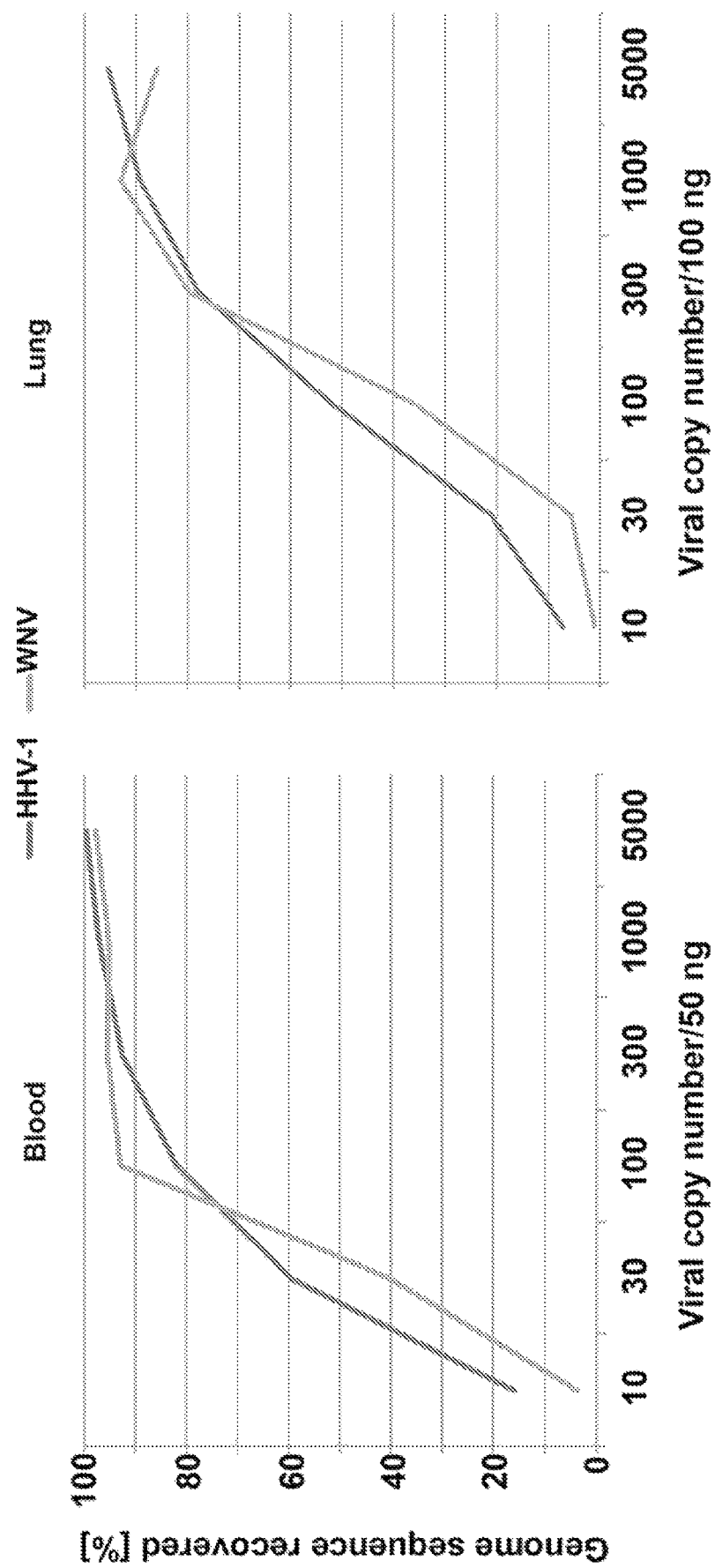
FIG. 4 are graphs depicting the limit of detection for VirCapSeq-VERT in percentage genome sequence recovered. Total nucleic acid from blood or lung tissue was spiked with human herpesvirus 1 (HHV-1) and West Nile virus (WNV) nucleic acid. The two preparations were serially diluted to generate six samples containing both viruses at 5000, 1000, 300, 100, 30, or 10 copies in 100 ng lung tissue or 50 ng whole blood nucleic acid. Samples were processed with VirCapSeq-VERT.
Figure 5:
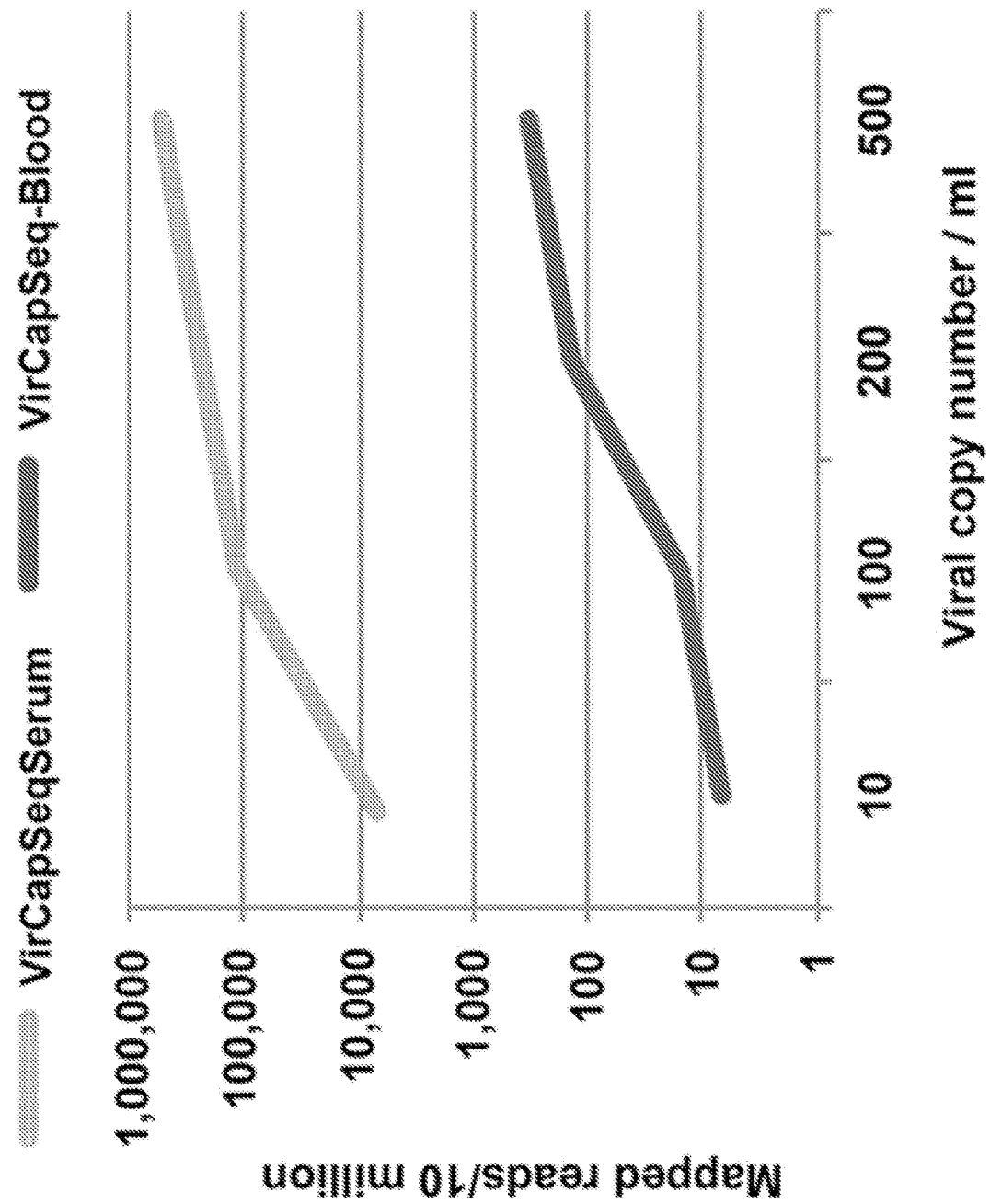
FIG. 5 is a graph depicting the efficiency of viral read mapping with VirCapSeq-VERT in mapped reads per ten million. Human blood and serum were spiked with live enterovirus D68 virus stock quantitated by qPCR to generate samples with 500, 200, 100 or 10 copies/ml. 500 μl of each sample were extracted and processed with VirCapSeq-VERT.

To determine the threshold for detection of viral sequence, NA from lung tissue homogenate and EDTA-blood that contained different amounts of WNV and herpes simplex virus 1 (HHV-1) NA was used. Nearly complete genome recovery (>90%) was achieved for both viruses at input levels of 100 viral copies in 50 ng of blood NA or 1,000 viral copies in 100 ng lung NA (FIG. 4). Extrapolated to clinical samples, these values correspond to a blood specimen containing approximately 1,200 copies/ml or a tissue specimen containing approximately 16,000 copies/mg, assuming 100% extraction yield (Table 5). Even at the lowest level of virus input tested, 10 viral copies per 50 ng background NA corresponding to approximately 100 copies copies/ml blood, VirCapSeq-VERT enabled recovery of 45 kb (29%) of HHV-1 and 0.75 kb (7%) of WNV genome sequence. Human blood and serum samples (1 ml) spiked with live enterovirus D68 (EV-D68) virus stock were tested. VirCapSeq-VERT enabled detection in both sample types at a concentration of 10 copies/ml (FIG. 5), comparable to the sensitivity of real time PCR (Table 6).

TABLE 3

Assessment of VirCapSeq-Vert Efficiency using Quantitated Viral Nucleic Acids to Spike Lung and Blood Host Nucleic Acid

| Pool | Host Background | Virus[b] | Load[a] | Library Preparation |
|---|---|---|---|---|
| 1a | 200 ng lung NA | FLUAV (Orthomyxoviridae); segmented negative-strand RNA, 13 kb/8 segments | $2 \times 10^4$ | Conventional HTS |
| | | MERS-CoV (Nidovirales, Coronaviridae); nonsegmented positive-strand RNA, 30 kb | $2 \times 10^4$ | |
| | | EV-D68 (Picornavirales, Picornaviridae); nonsegmented positive-strand RNA, 7 kb | $3 \times 10^5$ | |
| 1b | Same as pool 1a | Same as pool 1a | | Same as VirCapSeq-pool 1a VERT |
| 2a | 200 ng blood NA | DENV-3 (Flaviviridae); nonsegmented positive-strand RNA, 11 kb | $5 \times 10^5$ | |
| | | WNV (Flaviviridae); nonsegmented positive-strand RNA, 11 kb | $9 \times 10^3$ | |
| | | EBOV (Mononegavirales, Filoviridae); nonsegmented negative-strand RNA, 19k | $2 \times 10^3$ | |
| | | CVV (Bunyaviridae); segmented negative-strand RNA, 12 kb/ 3 segments | $8 \times 10^3$ | |
| | | HV-1 (Herpesvirales, Herpesviridae); nonsegmented double-strand DNA, 152 kb | $2 \times 10^5$ | |
| 2b | Same as pool 2a | Same as pool 2a | | Same as pool 2a |

[a]Determined by qPCR of double-stranded cDNA/DNA used for sequence library construction.
[b]FLUAV, influenza A virus H3N2; MERS-CoV, Middle East respiratory syndrome coronavirus; EV-D68, enterovirus D68; DENV-3, dengue virus 3; WNV, West Nile virus; EBOV, Ebola virus; CVV, Cache Valley virus; HHV-1, herpes simplex virus 1.

TABLE 4

VirCapSeq-VERT Provides Greater Genome Coverage and Sequencing Depth than HTS

| Library[b] | Virus | Load (copies)[a] | Genome length (nt) | No. of mapped positions | % sequence mapped | Coverage Min | Coverage Max | Coverage Avg | No. of unmapped regions | Unmapped region length (nt) |
|---|---|---|---|---|---|---|---|---|---|---|
| Pool 1a (lung, HTS) | EV-D68 | $10^5$ | 7,341 | 7,268 | 99.01 | 0 | 2,384 | 932 | 4 | 73 |
| | MERS-CoV | $10^4$ | 30,113 | 1,824 | 6.06 | 0 | 2 | 0.1 | 19 | 28,289 |
| | FLUAV-1 | $10^4$ | 2,316 | 2,005 | 86.57 | 0 | 9 | 2.5 | 5 | 311 |
| | FLUAV-2 | | 2,304 | 2,248 | 97.57 | 0 | 19 | 6.4 | 2 | 56 |
| | FLUAV-3 | | 2,208 | 1,998 | 90.49 | 0 | 29 | 3.8 | 4 | 210 |
| | FLUAV-4 | | 1,737 | 1,642 | 94.53 | 0 | 32 | 8.0 | 2 | 95 |
| | FLUAV-5 | | 1,540 | 1,494 | 97.01 | 0 | 14 | 4.1 | 3 | 46 |
| | FLUAV-6 | | 1,442 | 1,334 | 92.51 | 0 | 11 | 4.2 | 3 | 108 |
| | FLUAV-7 | | 1,002 | 948 | 94.61 | 0 | 11 | 3.7 | 2 | 54 |
| | FLUAV-8 | | 865 | 801 | 92.60 | 0 | 11 | 3.8 | 3 | 65 |
| Pool 1b (lung, VirCapSeq-VERT) | EV-D68 | $10^5$ | 7,341 | 7,341 | 100.00 | 3 | 8,080 | 7,005 | 0 | 0 |
| | MERS-CoV | $10^4$ | 30,113 | 29,020 | 96.37 | 0 | 121 | 13 | 23 | 1,093 |
| | FLUAV-1 | $10^4$ | 2,316 | 2,316 | 100.00 | 590 | 8,061 | 5,230 | 0 | 0 |
| | FLUAV-2 | | 2,304 | 2,304 | 100.00 | 569 | 8,048 | 7,608 | 0 | 0 |
| | FLUAV-3 | | 2,208 | 2,208 | 100.00 | 818 | 8,040 | 4,847 | 0 | 0 |
| | FLUAV-4 | | 1,737 | 1,737 | 100.00 | 323 | 8,038 | 7,449 | 0 | 0 |
| | FLUAV-5 | | 1,540 | 1,540 | 100.00 | 909 | 8,003 | 7,091 | 0 | 0 |
| | FLUAV-6 | | 1,442 | 1,442 | 100.00 | 348 | 7,999 | 6,975 | 0 | 0 |
| | FLUAV-7 | | 1,002 | 1,002 | 100.00 | 60 | 8,056 | 6,216 | 0 | 0 |
| | FLUAV-8 | | 865 | 865 | 100.00 | 448 | 8,006 | 5,761 | 0 | 0 |
| Pool 2a (blood, HTS) | HHV-1 | $10^5$ | 152,151 | 151,970 | 99.88 | 0 | 418 | 142 | 4 | 183 |
| | DENV-3 | $10^5$ | 10,707 | 10,687 | 99.81 | 0 | 1,242 | 622 | 1 | 20 |
| | WNV | $10^4$ | 10,945 | 500 | 4.57 | 0 | 1 | 0.1 | 16 | 10,445 |
| | EBOV | $10^3$ | 18,959 | 4,716 | 24.87 | 0 | 2 | 0.3 | 43 | 14,243 |
| | CVV-S | $10^4$ | 905 | 818 | 90.39 | 0 | 7 | 3.1 | 3 | 87 |
| | CVV-M | | 4,305 | 2,633 | 61.16 | 0 | 5 | 1.1 | 15 | 1,672 |
| | CVV-L | | 6,840 | 2,309 | 33.79 | 0 | 5 | 0.5 | 17 | 4,531 |

TABLE 4-continued

VirCapSeq-VERT Provides Greater Genome Coverage and Sequencing Depth than HTS

| Library[b] | Virus | Load (copies)[a] | Genome length (nt) | No. of mapped positions | % sequence mapped | Coverage Min | Coverage Max | Coverage Avg | No. of unmapped regions | Unmapped region length (nt) |
|---|---|---|---|---|---|---|---|---|---|---|
| Pool 2b | HHV-1 | $10^5$ | 152,151 | 152,133 | 99.99 | 0 | 8,001 | 5,373 | 1 | 18 |
| (blood, | DENV-3 | $10^5$ | 10,707 | 10,688 | 99.82 | 0 | 8,068 | 7,774 | 1 | 19 |
| VirCapSeq- | WNV | $10^4$ | 10,945 | 10,428 | 95.28 | 0 | 214 | 66 | 1 | 517 |
| VERT) | EBOV | $10^3$ | 18,959 | 16,413 | 86.57 | 0 | 394 | 56 | 11 | 2,546 |
|  | CVV-S | $10^4$ | 905 | 904 | 99.89 | 0 | 7,319 | 2,302 | 1 | 1 |
|  | CVV-M |  | 4,305 | 4,305 | 100.00 | 2 | 1,551 | 401 | 0 | 0 |
|  | CVV-L |  | 6,840 | 6,840 | 100.00 | 1 | 858 | 88 | 0 | 0 |

[a]Determined by qPCR of double-stranded-cDNA/DNA used for sequence library construction.
[b]See Table 3 for pool composition.

TABLE 5

Estimation of the Limit of Detection Achieved By VirCapSEq-VERT using Nucleic Acid Extracts

| Load * | Virus equivalents/ml blood or/mg tissue # | % genome sequenced blood HHV-1 | % genome sequenced blood WNV | % genome sequenced lung HHV-1 | % genome sequenced lung WNV |
|---|---|---|---|---|---|
| 5000 | 60,000/80,000 | 99.6 | 97.8 | 95.4 | 85.9 |
| 1000 | 12,000/16,000 | 97.2 | 95.1 | 89.3 | 92.9 |
| 300 | 3,600/4,800 | 92.6/97.3 [$] | 95.6/95.7 | 77.7/87.0 | 79.7/92.3 |
| 100 | 1,200/1,600 | 82.0/91.3 | 93.1/93.9 | 51.9/69.0 | 35.8/52.2 |
| 30 | 360/480 | 59.7/73.4 | 40.6/56.7 | 21.0/33.3 | 5.5/6.3 |
| 10 | 120/160 | 16.1/29.4 | 3.8/6.9 | 7.1/8.4 | 0.9/0.9 |

* Virus nucleic acid copies quantitated by qPCR and added to 50 nanograms blood or 100 nanograms lung derived background nucleic acid used for sequencing library construction
assuming 100% yield of extraction
$ all 6 samples were capture hybridized together (with different bar-codes)/each sample was capture hybridized individually

TABLE 6

Estimation of the Limit of Detection Achieved by VirCapSeq-VERT using Live Enterovirus D68

| Load [/ml] | EV-D68 in serum qPCR [copies/ds cDNA] | EV-D68 in serum No. mapped reads * | EV-D68 in serum % genome sequenced | EV-D68 in blood qPCR [copies/ds cDNA] | EV-D68 in blood No. mapped reads * | EV-D68 in blood % genome sequenced |
|---|---|---|---|---|---|---|
| 500 | 192 | 3,742,035 | 98.9 | 11 | 2,358 | 82.3 |
| 200 | 81 | 1,752,524 | 97 | 4 | 982 | 71.3 |
| 100 | 51 | 839,868 | 98.2 | n.d. | 119 | 23.2 |
| 10 | 2 | 45,888 | 90 | n.d. | 34 | 8.2 |

* per 10,000,000 total reads

Example 4

Comparison with Other Enrichment Regimens

Analysis of samples of human blood spiked with live EV-D68, HHV-1 and influenza A virus (FLUAV) stock indicated that VirCapSeq-VERT yielded an up to 10,000-fold increase in mapped read counts over samples treated after extraction with DNase and RiboZero rRNA depletion, individually or in combination, and then processed by standard HTS. VirCapSeq-VERT resulted in nearly full genome recovery for most viruses even with less than 1,000 copies of target input (Table 7).

Clinical specimens included a human nasal swab sample containing EV-D68 that was divided into three aliquots treated with (i) filtration and nuclease digestion prior to extraction and standard HTS, (ii) filtration and nuclease digestion prior to extraction and VirCapSeq-VERT, or (iii) no treatment prior to extraction and VirCapSeq-VERT. VirCapSeq-VERT with no prior treatment enabled the highest sequence recovery and depth (Table 8).

Since fecal material is frequently challenging for viromic analyses, a sample of fecal pellets from bats known to contain rotavirus sequences was tested. The sample was divided into four aliquots and treated with (i) filtration and nuclease digestion prior to extraction, followed by standard HTS, (ii) filtration and nuclease digest prior to extraction, followed by DNase digestion after extraction and standard HTS, (iii) filtration and nuclease digestion prior to extraction and VirCapSeq-VERT, or (iv) no treatment prior to extraction and VirCapSeq-VERT. VirCapSeq-VERT again yielded the highest mapped read count (Table 9).

Figure 6:
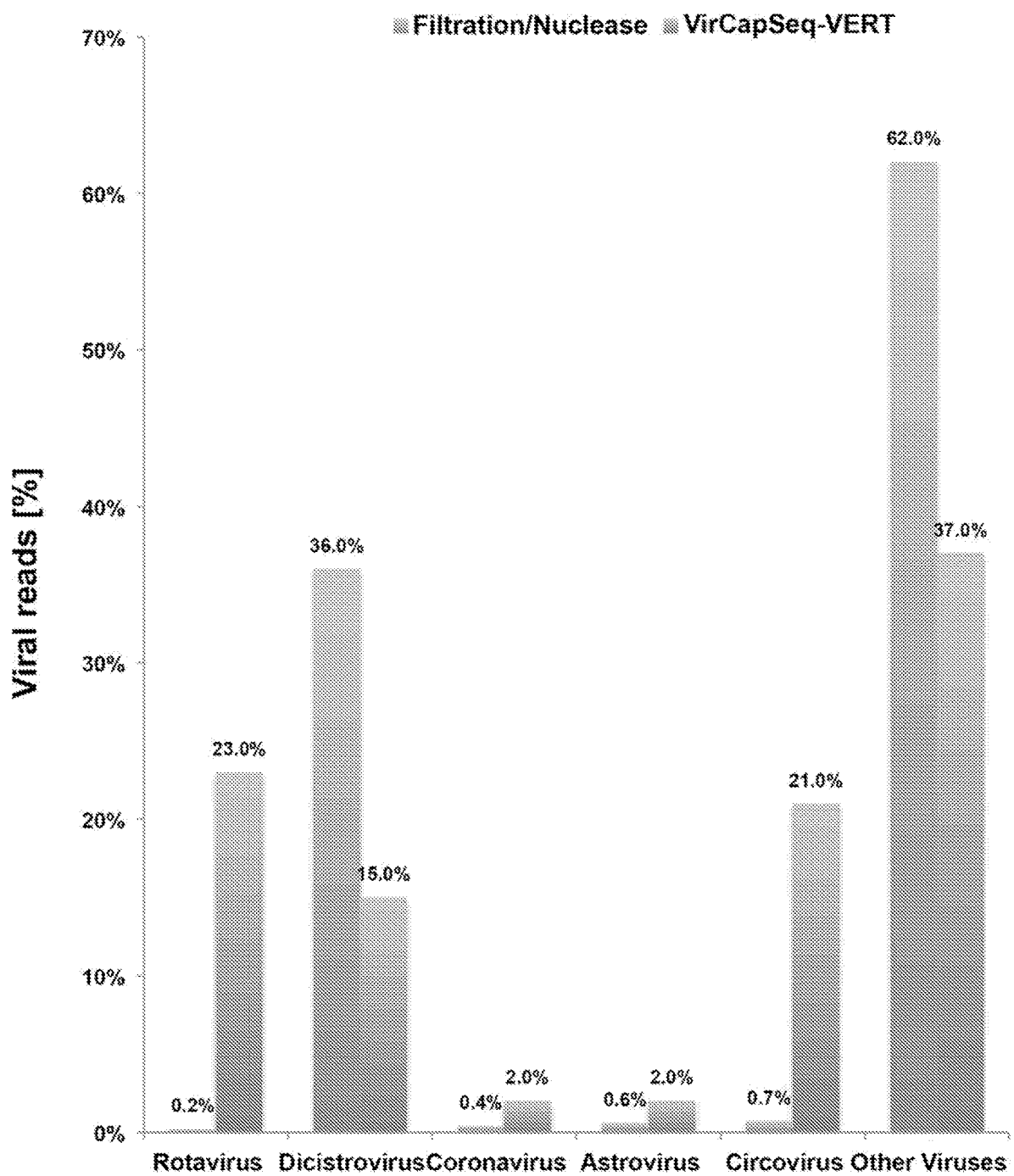
FIG. 6 is a graph showing the selective enhancement of vertebrate virus detection by VirCapSeq-VERT in percent of viral reads. Bat fecal sample material was divided into two and analyzed using HTS with filtration and nuclease digest combined with post-extraction DNase treatment (left hand bars of the graph), or using VirCapSeq-VERT alone (right hand bars of the graph) for each virus.

The specificity of VirCapSeq-VERT for relevant targets was readily apparent in comparison with results obtained by conventional HTS. Whereas up to 36% of the viral reads found by conventional HTS represented insect-infecting dicistroviruses, these reads were reduced to 15% by VirCapSeq-VERT. Vertebrate rotavirus, coronavirus, astrovirus and circovirus sequences detected only at low levels in conventional HTS were increased approximately 10-fold by VirCapSeq-VERT (FIG. 6).

Since the precise sequence of the rotavirus present in bat samples was unknown, contigs obtained by de novo assembly were used to identify the closest GenBank match of each segment. Table 9 shows that nearly full sequence was obtained for sequences differing by up to 25% from the known sequences used for VirCapSeq-VERT probe design. Partial sequence in conserved regions was obtained even for sequences differing by as much as 50% from known sequences (NSP1 and NSP4, Table 10).

TABLE 7

VirCapSeq-VERT Performance Compared to Conventional Enrichment Procedures

| Treatment (preparation)a | Virus load (copies)[b](HHV/FLUAV/EV) | No. of reads | No. of reads (total/normalized[d]) | | | |
|---|---|---|---|---|---|---|
| | | | Viral | Mapped to virus | | |
| | | | | HHV-1 | FLUAV | EV-D68 |
| DNase (conventional) | $6 \times 10^2$/ND/$9 \times 10^2$ | 20,449,329 | 219/107 | 59/29[c] | 6/3 | 154/75 |
| RiboZero (conventional) | $2 \times 10^3$/$8 \times 10^2$/$2 \times 10^3$ | 82,866,269 | 4,251/513 | 2,951/356 | 39/5 | 1,261/152 |
| DNase/RiboZero (conventional) | ND/ND/$2 \times 10^3$ | 68,239,834 | 3,927/576 | 6/0.9[c] | 3/0.4 | 3,918/575 |
| None (conventional) | $2 \times 10^4$/$3 \times 10^4$/$2 \times 10^4$ | 121,961,881 | 4,562/374 | 2,569/211 | 65/5 | 1,928/158 |
| None (VirCapSeq-VERT) | $2 \times 10^4$/$2 \times 10^4$/$2 \times 10^4$ | 128,764,130 | 2,773,382/215,325 | 713,557/55,400 | 572,169/44,423 | 1,487,656/115,501 |
| None (VirCapSeq-VERT)[e] | $9 \times 10^2$/$8 \times 10^2$/$9 \times 10^2$ | 64,989,060 | 86,943/13,376 | 21,631/3,328 | 19,255/2,962 | 46,057/7,086 | aHuman blood was spiked with live virus stocks derived from tissue culture to result in approximately $10^4$ copies of herpes simplex virus 1 (HHV-1), influenza A virus (FLUAV), and enterovirus D68 (EV-D68) per 250 ng extracted blood NA. The sample was divided into equivalent aliquots to be processed with the indicated treatment prior to RT reaction and subjected to either conventional sequence library preparation or VirCapSeq-VERT.
[b]Determined by qPCR of double-stranded cDNA/DNA used for sequence library construction.
[c]HHV-1 detection was impaired due to DNase.
[d]Normalized to 10,000,000 total reads.
[e]Prepared with additional dilution of the sample in a blood background.

TABLE 8

Efficiency of Enterovirus D68 (EV-D68) Detection and Genome Sequencing in Nasal Swab using VirCapSEQ-VERT or other Methods for Viral Template Enrichment

| | Treatment * | | Reads | Reads mapped to EV-D68 total/normalized [#] | % genome mapped | Average coverage | No. of unmapped regions | Unmapped region length [nt] |
|---|---|---|---|---|---|---|---|---|
| i | filtration, nuclease | HTS | 35,590,447 | 1/0.3 | 1.4 | 0 | 2 | 7,241 |
| ii | filtration, nuclease | VirCapSeq | 181,508,633 | 784/43 | 77.4 | 11 | 19 | 1,656 |
| iii | none | VirCapSeq | 67,438,157 | 1,398/207 | 93.9 | 19 | 7 | 445 |

* Nasal swab sample containing approx. $3 \times 10^2$ EV-D68 copies was used for each treatment (measured by qPCR)
[#] Normalized to 10,000,000 total reads

TABLE 9

Efficiency of Rotavirus Detection and Genome Sequencing in Bat Feces using VirCapSEQ-VERT or other Methods for Viral Template Enrichment

| | Treatment * | | Reads | Reads mapped total/normalized [#] |
|---|---|---|---|---|
| i | filtration, nuclease | HTS | 45,850,963 | 0/0 |
| ii | filtration, nuclease, DNase | HTS | 51,032,706 | 1,809/355 |
| iii | filtration, nuclease | VirCapSeq | 84,145,481 | 84,118/9,997 |
| iv | none | VirCapSeq | 40,070,879 | 168,208/41,978 |

[#] Normalized to 10,000,000 total reads

TABLE 10

Capacity of VirCapSeq-VERT to Detect Divergent Sequences

| Rotavirus gene | Sequence length (nt) | % mapped | Closest BLASTN hit identity (%) |
|---|---|---|---|
| VP1 | 3,280 | 97 | 78 |
| VP2 | 2,712 | 99 | 93 |
| VP3 | 2,592 | 86 | 78 |
| VP4 | 2,362 | 97 | 75 |
| NSP1 | 1,614 | 40 | 53 |
| VP6 | 1,194 | 92 | 96 |
| NSP3 | 1,075 | 95 | 76 |
| NSP2 | 954 | 88 | 96 |
| VP7 | 982 | 93 | 82 |
| NSP4 | 528 | 19 | 47 |
| NSP5 | 630 | 97 | 95 |

Example 5

Detection of Novel Sequences

To further test the capacity of VirCapSeq-VERT to detect novel viral sequences, an extract of a liver homogenate from a deer mouse experimentally infected with the rodent hepacivirus isolate RHVpl-01 was used. The complete genome sequence of this isolate has a less than 65% global nt sequence identity with the sequences used to design the VirCapSeq-VERT probes. Nonetheless, VirCapSeq-VERT selectively enriched RHVpl-01 sequence in conserved regions encoding the helicase and polymerase genes wherein bioinformatics analysis showed the presence of probes with up to 90% nt identity in the VirCapSeq-VERT probe pool.

Pool-2 contained the same 9 samples mixed with the remaining 14 samples. All viruses in the 9-plex as well as in the 23-plex sample pool were efficiently characterized (FIG. 7).

TABLE 11

Genome Mapping and Coverage in VirCapSeq-VERT Multiplex Assays

| | 7-plex mix[a] | | | 21-plex mix | | | | | | | | |
|---|---|---|---|---|---|---|---|---|---|---|---|---|
| Virus | Load (copies) | % genome mapped | Avg coverage | Load (copies) | % genome mapped | Avg coverage | Load (copies) | % genome mapped | Avg coverage | Load (copies) | % genome mapped | Avg coverage |
| HHV-1 | $10^4$ | 100 | 4,258 | $10^4$ | 99.6 | 583 | $10^6$ | 99.9 | 5,438 | $10^2$ | 84.5 | 10 |
| MERS-CoV | $10^4$ | 27.9 | 1.1 | $10^4$ | 20.1 | 0.34 | $10^6$ | 98.7 | 23 | $10^2$ | 0.3 | 0 |
| WNV | $10^4$ | 98.8 | 4,785 | $10^4$ | 98.9 | 251 | $10^8$ | 100 | 7,799 | $10^2$ | 99.1 | 107 |
| EBOV | $10^4$ | 98.9 | 3,019 | $10^4$ | 97.9 | 643 | $10^5$ | 99.9 | 5,010 | $10^2$ | 83.6 | 7 |
| EV-D68 | $10^4$ | 99.9 | 6,644 | $10^4$ | 99.8 | 4,816 | $10^6$ | 99.9 | 6,911 | $10^2$ | 91.8 | 64 |
| CVV-S | $10^4$ | 100 | 6,197 | $10^4$ | 100 | 2,364 | $10^7$ | 100 | 7,332 | $10^2$ | 99.8 | 49 |
| CVV-M | $10^4$ | 100 | 7,603 | $10^4$ | 100 | 1,048 | $10^7$ | 100 | 7,798 | $10^2$ | 100 | 23 |
| CVV-L | $10^4$ | 100 | 2,409 | $10^4$ | 100 | 242 | $10^7$ | 100 | 7,735 | $10^2$ | 93.4 | 4 |
| FLUAV-1 | $10^4$ | 100 | 7,818 | $10^4$ | 100 | 7,633 | $10^5$ | 100 | 7,892 | $10^2$ | 100 | 238 |
| FLUAV-2 | $10^4$ | 100 | 7,904 | $10^4$ | 100 | 7,741 | $10^5$ | 100 | 7,902 | $10^2$ | 100 | 575 |
| FLUAV-3 | $10^4$ | 100 | 7,792 | $10^4$ | 100 | 7,658 | $10^5$ | 100 | 7,906 | $10^2$ | 100 | 276 |
| FLUAV-4 | $10^4$ | 100 | 7,800 | $10^4$ | 100 | 7,584 | $10^5$ | 100 | 7,799 | $10^2$ | 100 | 594 |
| FLUAV-5 | $10^4$ | 100 | 7,747 | $10^4$ | 100 | 7,605 | $10^5$ | 100 | 7,746 | $10^2$ | 100 | 352 |
| FLUAV-6 | $10^4$ | 100 | 7,721 | $10^4$ | 100 | 7,560 | $10^5$ | 100 | 7,721 | $10^2$ | 100 | 358 |
| FLUAV-7 | $10^4$ | 100 | 7,355 | $10^4$ | 100 | 7,100 | $10^5$ | 100 | 7,711 | $10^2$ | 100 | 251 |
| FLUAV-8 | $10^4$ | 100 | 7,367 | $10^4$ | 100 | 7,360 | $10^5$ | 100 | 7,367 | $10^2$ | 100 | 397 |

[a] qPCR quantitated nucleic acid extracts representing seven different viruses were used to spike a background of human blood nucleic acid at levels of approximately $10^4$ copies/100 ng, $10^2$ copies/100 ng, and $10^5$ to $10^8$ copies/100 ng. Individual sequence libraries were prepared using 21 different indexes for bar coding. Libraries were mixed for capture hybridization into a 7-plex mix (libraries prepared from $10^4$ loads) and the complete 21-plex mix.

Therefore, it was concluded from rotavirus and hepacivirus experiments that VirCapSeq-VERT can detect novel viruses through hybridization to short conserved sequence motifs within larger genome fragments.

Example 6

Sample Multiplexing

During the estimation of the limit of detection (LoD) of VirCapSeq-VERT, samples were processed samples individually or together during hybridization capture. The results obtained were superior with the samples processed individually (Table 5). This finding suggested that competition for probe populations may compromise application in diagnostic settings where patient samples may have widely divergent virus loads. The practical impact of this potential confound was investigated in assays using 21 barcoded libraries representing samples containing seven different viruses at genome loads that varied from $10^2$ to $10^8$. One set represented the seven different viruses each at a concentration of approximately $10^4$ genome copies/library. To mimic competition anticipated in some clinical samples, the second set contained the same seven libraries at $10^4$ copies, combined with an additional 14 libraries prepared with the seven viruses at $10^2$ and at $10^5$-$10^8$ copies. Virus detection was not impaired in multiplex assays even with samples that varied up to $10^4$ in target concentration (Table 11); however, genome coverage was typically higher in 7-plex than in 21-plex assays.

To determine the utility of VirCapSeq-VERT in characterization of virome diversity and dynamics, a set of 23 serum samples collected from multiply transfused hemophilia patients known to contain hepatitis C virus (HCV), GB virus C (GBV-C), human immunodeficiency virus (HIV) and torque teno virus (TTV) were used. Samples were amplified using unique barcodes and two pools were generated for VirCapSeq-VERT. Pool-1 contained 9 samples.

REFERENCES

Alva et al. (2016) The MPI bioinformatics Toolkit as an integrative platform for advanced protein sequence and structure analysis. Nucleic Acids Research. pii: gkw348. PMID: 27131380).

Bent et al. 2013. Enriching pathogen transcripts from infected samples: a capture-based approach to enhanced host-pathogen RNA sequencing. Anal Biochem 438:90-96.

Briese et al. 2005. Diagnostic system for rapid and sensitive differential detection of pathogens. Emerg Infect Dis 11:310-313.

Brown et al. 2014. Seven strains of enterovirus D68 detected in the United States during the 2014 severe respiratory disease outbreak. Genome Announc 2:e01201-14.

Chevreux et al. 1999. Genome sequence assembly using trace signals and additional sequence information. Comput Sci Biol 99:45-56.

Clark et al. 2015. Quantitative gene profiling of long noncoding RNAs with targeted RNA sequencing. Nature Methods 12:339-342.

Depledge et al. 2011. Specific capture and whole-genome sequencing of viruses from clinical samples. PLoS One 6:e27805.

Drexler et al. 2014. Robustness against serum neutralization of a poliovirus type 1 from a lethal epidemic of poliomyelitis in the Republic of Congo in 2010. Proc Natl Acad Sci U S A 111:12889-12894.

Edgar 2010 Search and clustering orders of magnitude faster than BLAST. Bioinformatics 26(19):2460-2461.

Finn et al. 2011 HMMER Web Server: Interactive Sequence Similarity Searching. Nucleic Acids Research 39:W29-37.

Guillot et al. 1994. Point mutations involved in the attenuation/neurovirulence alternation in type 1 and 2 oral polio vaccine strains detected by site-specific polymerase chain reaction. Vaccine 12:503-507.

Kapoor and Lipkin 2001. Virus discovery in the 21st century. In eLS. John Wiley & Sons, New York, N.Y.

Kapoor et al. 2013. Identification of rodent homologs of hepatitis C virus and pegiviruses. *mBio* 4:e00216-13.

Li and Godzik 2006. Cd-hit: a fast program for clustering and comparing large sets of protein or nucleotide sequences. *Bioinformatics* 22:1658-1659.

Li et al., 1000 Genome Project Data Processing Subgroup. 2009. The Sequence Alignment/Map format and SAMtools. *Bioinformatics* 25:2078-2079.

Luo et al. 2012. SOAPdenovo2: an empirically improved memory-efficient short-read de novo assembler. *Gigascience* 1:18.10.1186/2047-217X-1-18.

Mercer et al. 2014. Targeted sequencing for gene discovery and quantification using RNA CaptureSeq. *Nature Protocols* 9:989-1009.

Mullis and Faloona 1987. Specific synthesis of DNA in vitro via a polymerase-catalyzed chain reaction. *Methods Enzymology* 155:335-350.

Palacios et al. 2007. Panmicrobial oligonucleotide array for diagnosis of infectious diseases. *Emerg Infect Dis* 13:73-81.

Robinson et al. 2011. Integrative genomics viewer. *Nat Biotechnol* 29:24-26.

Saeed et al. 2003. TM4: a free, open-source system for microarray data management and analysis. *Biotechniques* 34:374-378.

Schmieder and Edwards 2011. Quality control and preprocessing of metagenomic datasets. *BioInformatics* 27:863-864.

Tokarz et al. 2012. Worldwide emergence of multiple clades of enterovirus 68. *J Gen Virol* 93:1952-1958.

UniProt Consortium 2015 UniProt: a Hub for protein information. *Nucleic Acids Research* 43:D204-D212.

Wang et al. 2002. Microarray-based detection and genotyping of viral pathogens. *Proc Natl Acad Sci U S A* 99:15687-15692.

The invention claimed is:

1. A method of constructing a virome capture sequencing platform comprising oligonucleotides for the simultaneous detection, identification and/or characterization of all viruses known or suspected to infect vertebrates, comprising:
   a. obtaining nucleotide sequences of the genomes of at least one virus in each of the viral taxa listed in Table 1;
   b. extracting coding sequences from the nucleotide sequences obtained in step a, wherein coding sequences clustered at least about 80% identity are chosen for extraction;
   c. breaking the coding sequences into fragments, wherein the fragments are 50 to 100 nucleotides in length, have about 90% sequence identity, and are tiled across the coding sequences at specific intervals to obtain sequence information to design oligonucleotides that selectively hybridize to genomes of all viruses that infect or are suspected of infecting vertebrates; and
   d. synthesizing the oligonucleotides for which the sequence information was obtained in step c.

2. The method of claim 1, wherein the length of the fragments are adjusted such that the melting temperatures of all of the fragments are in a range of about no greater than 75° C.

3. The method of claim 1, wherein the length of the fragments are adjusted such that the melting temperatures of all of the fragments are in a range of about no greater than 50° C.

4. The method of claim 1, wherein the intervals of which the fragments are tiled across the coding sequences are 25 to 50 nucleotides in length.

5. The method of claim 1, wherein the oligonucleotides are chosen from the group consisting of DNA, RNA, Bridged Nucleic Acids, Locked Nucleic Acids, and Peptide Nucleic Acids.

6. The method of claim 1, wherein the oligonucleotides are synthesized on a cleavable microarray.

7. The method of claim 1, wherein the oligonucleotides are modified to comprise a composition for binding to a solid support, chosen from the group consisting of biotin, digoxygenin, ligands, small organic molecules, small inorganic molecules, apatamers, antigens, antibodies, and substrates.

8. The method of claim 1, wherein coding sequences clustered at about 90% identity are chosen for extraction.

9. The method of claim 1, wherein coding sequences clustered at about 96% identity are chosen for extraction.

10. A virome capture sequencing platform for the simultaneous detection, identification and/or characterization of all viruses known or suspected to infect vertebrates, constructed by steps a-c of the method of claim 1, wherein the platform is in the form of a database recorded on a non-transitory machine-readable storage medium comprising sequence information, length, melting temperature, and viral origin of each oligonucleotide for which sequence information was obtained in step c.

11. A virome capture sequencing platform for the simultaneous detection, identification and/or characterization of all viruses known or suspected to infect vertebrates, constructed by the method of claim 1, wherein the platform is in the form of an oligonucleotide library in a cleavable array format.

12. The virome capture sequencing platform of claim 11 wherein the oligonucleotides are linked to biotin and bound to a cleavable array.

13. A method of simultaneously detecting the presence of all viruses known or suspected to infect vertebrates in a sample, comprising:
   a. isolating nucleic acid from the sample;
   b. contacting the nucleic acid with oligonucleotides of the virome capture sequencing platform of claim 11 to form hybridization products;
   c. detecting hybridization products between the nucleic acids from the sample and the oligonucleotides;
      wherein the presence of the hybridization product with an oligonucleotide originating from a particular virus indicates the presence of the virus in the sample.

14. The method of claim 13, wherein the sample is chosen from the group consisting of a biological sample, an environmental sample, and a food sample.

15. The method of claim 13, wherein the sample is from a human subject.

16. The method of claim 13, wherein the sample is blood being tested prior to transfusion.

17. The method of claim 13, wherein the sample is chosen from the group consisting of cells, cell culture, cell culture medium and other compositions being used for the development of pharmaceutical and therapeutic agents.

18. The method of claim 13, further comprising the steps of: sequencing any hybridization products between the nucleic acids from the sample and the oligonucleotides; comparing the nucleotide sequence of the hybridization products to the nucleotide sequences of known viruses; and identifying and characterizing the virus by the identity between the sequence of the hybridization product and sequences of known viruses and wherein the virus is considered novel if there is no identity between the sequence of the hybridization product and sequences of known viruses.

19. A kit for detecting, identifying and characterizing all viruses that infect or are suspected to infect vertebrates comprising the virome capture sequencing platform of claim 10.

20. A kit for detecting, identifying and characterizing all viruses that infect or are suspected to infect vertebrates comprising the virome capture sequencing platform of claim 11.

21. The kit of claim 20, wherein the oligonucleotides are linked to biotin and bound to a cleavable array.

22. A computer program product stored on a memory device adapted to cause a computer to carry out a method of designing and/or constructing a virome capture sequencing platform comprising oligonucleotides for the simultaneous detection, identification and/or characterization of all viruses known or suspected to infect vertebrates, comprising:

a. obtaining nucleotide sequences of the genomes of at least one virus in each of the viral taxa listed in Table 1;

b. extracting coding sequences from the nucleotide sequences obtained in step a, wherein coding sequences clustered at least about 80% identity are chosen for extraction; and c. breaking the coding sequences into fragments, wherein the fragments are 50 to 100 nucleotides in length, have about 90% sequence identity, and are tiled across the coding sequences at specific intervals to obtain sequence information to design oligonucleotides that selectively hybridize to genomes of all viruses that infect or are suspected of infecting vertebrates and d. outputting the virome capture sequencing platform comprising oligonucleotides with sequence information, length, melting temperature, and viral origin of each oligonucleotide for which sequence information was obtained in step c.

\* \* \* \* \*